US007270959B2

(12) United States Patent
Hudak

(10) Patent No.: US 7,270,959 B2
(45) Date of Patent: *Sep. 18, 2007

(54) SPECIMEN COLLECTION CONTAINER

(75) Inventor: Robert Thomas Hudak, Carlsbad, CA (US)

(73) Assignee: Oakville Hong Kong Company Limited, Hong Kong (HK)

( * ) Notice: Subject to any disclaimer, the term of this patent is extended or adjusted under 35 U.S.C. 154(b) by 370 days.

This patent is subject to a terminal disclaimer.

(21) Appl. No.: 09/915,494

(22) Filed: Jul. 25, 2001

(65) Prior Publication Data

US 2003/0022392 A1 Jan. 30, 2003

(51) Int. Cl.
*G01N 33/53* (2006.01)

(52) U.S. Cl. .................. 435/7.1; 435/7.92; 435/287.7; 422/102; 422/103; 422/104; 422/58

(58) Field of Classification Search .................. 422/55, 422/58, 68.1, 102, 103, 104, 81, 82; 435/7.1, 435/7.92–7.94, 287.7, 287.9; 436/518, 164, 436/165, 169; 73/864.32, 864.63, 864.91
See application file for complete search history.

(56) References Cited

U.S. PATENT DOCUMENTS

| 228,031 A | 5/1880 | Broughton |
| 424,982 A | 4/1890 | Hidden |
| 645,430 A | 3/1900 | Smelker |
| 711,452 A | 10/1902 | Meyer |
| D140,925 S | 4/1945 | Christner et al. ............ D58/13 |
| 3,000,540 A | 9/1961 | Wheeler |
| 3,658,216 A | 4/1972 | Schwartzman et al. |
| 3,687,333 A | 8/1972 | Burnett et al. |

(Continued)

FOREIGN PATENT DOCUMENTS

EP          0250137 A2     6/1987

(Continued)

OTHER PUBLICATIONS

"Is he using drugs?" ACON Product brochure, 2003.

(Continued)

*Primary Examiner*—Long V. Le
*Assistant Examiner*—Gary W. Counts
(74) *Attorney, Agent, or Firm*—Fish & Richardson P.C.; Fred C. Hernandez

(57) ABSTRACT

The present invention recognizes that sample handling devices, particularly those used for testing for substances of abuse, do not allow for a separation of the bulk sample from a sample thereof to be tested. The present invention provides such a device and methods of use. The present invention includes but is not limited to a specimen collection device that includes a chamber such that the chamber is capable of collecting a specimen. The device also includes a reservoir such that the reservoir is capable of receiving a portion of the specimen from the chamber and optionally so that the reservoir is capable of receiving a test device. The device includes a valve functionally interposed between the chamber and the reservoir that is capable of transferring at least a portion of the specimen from the chamber to the reservoir such that the chamber and the reservoir are not in direct fluid communication. The device optionally includes a means for fluidic communication between the chamber, the valve and the reservoir.

28 Claims, 4 Drawing Sheets

U.S. PATENT DOCUMENTS

| | | | |
|---|---|---|---|
| 3,688,942 A | 9/1972 | Mitchell et al. | |
| 3,723,064 A | 3/1973 | Liotta | 23/230 |
| 3,837,518 A | 9/1974 | Gach | |
| 3,951,748 A | 4/1976 | Devlin | 195/103.5 |
| 3,990,850 A | 11/1976 | Friedman et al. | 435/287.9 |
| 3,990,853 A | 11/1976 | Godin | 422/100 |
| 3,991,055 A * | 11/1976 | Godin et al. | 23/259 |
| 4,024,976 A | 5/1977 | Acton | |
| 4,087,326 A | 5/1978 | Kereluk | 195/103.5 |
| 4,087,332 A | 5/1978 | Hansen | 195/127 |
| 4,111,329 A | 9/1978 | Lampman | |
| D250,129 S | 10/1978 | Skinner | D24/56 |
| 4,133,639 A | 1/1979 | Harte | 23/230 |
| 4,165,018 A | 8/1979 | Giggard | |
| 4,177,930 A | 12/1979 | Crisci | |
| 4,190,175 A | 2/1980 | Allen | |
| 4,205,043 A | 5/1980 | Esch et al. | 422/56 |
| 4,211,749 A * | 7/1980 | Kantner | 422/102 |
| 4,237,234 A | 12/1980 | Meunier | |
| 4,244,916 A | 1/1981 | Guigan | 422/72 |
| D258,311 S | 2/1981 | Peterson | D24/54 |
| 4,270,921 A | 6/1981 | Graas | 23/230 |
| 4,275,149 A | 6/1981 | Litman et al. | |
| 4,298,345 A | 11/1981 | Sodickson et al. | 23/230 |
| 4,299,916 A | 11/1981 | Litman et al. | |
| 4,301,139 A | 11/1981 | Feingers et al. | 424/1 |
| 4,313,734 A | 2/1982 | Leuvering | 23/230 |
| 4,323,536 A | 4/1982 | Columbus | 422/56 |
| 4,338,094 A | 7/1982 | Elahi | 23/230 |
| 4,361,537 A | 11/1982 | Deutsch et al. | 422/56 |
| 4,366,241 A | 12/1982 | Tom et al. | 435/7 |
| 4,376,110 A | 3/1983 | David et al. | 436/54 |
| 4,391,904 A | 7/1983 | Litman et al. | 435/7 |
| 4,394,944 A | 7/1983 | Rech | |
| 4,421,244 A | 12/1983 | Van Melle | |
| 4,425,438 A | 1/1984 | Bauman et al. | 436/527 |
| 4,426,451 A | 1/1984 | Columbus | 436/518 |
| 4,435,504 A | 3/1984 | Zuk et al. | 435/7 |
| 4,446,232 A | 5/1984 | Liotta | 435/7 |
| 4,462,510 A | 7/1984 | Steer | |
| 4,474,892 A | 10/1984 | Murad et al. | 436/54 |
| 4,476,993 A | 10/1984 | Krout | |
| 4,485,938 A | 12/1984 | Williams | 221/154 |
| 4,493,432 A | 1/1985 | Smith | 222/270 |
| 4,512,493 A | 4/1985 | Von Holdt | |
| 4,517,288 A | 5/1985 | Giegel et al. | 435/7 |
| 4,535,057 A | 8/1985 | Dreesman et al. | 435/5 |
| 4,646,926 A | 3/1987 | Agbay et al. | |
| 4,657,027 A | 4/1987 | Paulsen | 600/575 |
| 4,659,678 A | 4/1987 | Forrest et al. | 436/512 |
| 4,666,863 A | 5/1987 | Edwards et al. | 436/514 |
| D290,136 S | 6/1987 | Ball et al. | D24/9 |
| 4,673,657 A | 6/1987 | Christian | 436/501 |
| 4,678,757 A | 7/1987 | Rapkin et al. | 436/169 |
| 4,680,270 A * | 7/1987 | Mitsumaki et al. | 436/52 |
| 4,696,797 A | 9/1987 | Kelton | 422/101 |
| 4,700,860 A | 10/1987 | Li | |
| 4,703,017 A | 10/1987 | Campbell et al. | 436/532 |
| 4,711,364 A | 12/1987 | Leticia | |
| 4,718,571 A | 1/1988 | Bordner | |
| 4,722,458 A | 2/1988 | Van Dal | |
| 4,725,406 A | 2/1988 | Compton et al. | 422/58 |
| 4,740,468 A | 4/1988 | Weng et al. | 435/7 |
| 4,752,448 A | 6/1988 | Wells et al. | 422/56 |
| 4,769,215 A | 9/1988 | Ehrenkranz | |
| D299,744 S | 2/1989 | Bauer | D24/17 |
| 4,806,311 A | 2/1989 | Greenquist | 422/56 |
| 4,806,487 A | 2/1989 | Akers et al. | 436/93 |
| 4,807,771 A | 2/1989 | Roy et al. | |
| 4,837,168 A | 6/1989 | de Jaeger et al. | 436/533 |
| 4,852,560 A | 8/1989 | Hermann, Jr. et al. | 600/575 |
| 4,853,335 A | 8/1989 | Olsen et al. | 436/527 |
| 4,855,240 A | 8/1989 | Rosenstein et al. | 436/514 |
| 4,857,453 A | 8/1989 | Ullman et al. | 435/7 |
| 4,886,184 A | 12/1989 | Chamourian | |
| 4,900,663 A | 2/1990 | Wie et al. | 435/7 |
| 4,909,933 A * | 3/1990 | Carter et al. | 210/95 |
| 4,923,680 A | 5/1990 | Nelson | 422/58 |
| 4,938,927 A | 7/1990 | Kelton et al. | 422/64 |
| 4,943,522 A | 7/1990 | Eisinger et al. | 435/7 |
| 4,952,517 A | 8/1990 | Bahar | 436/518 |
| 4,954,452 A | 9/1990 | Yost et al. | 436/524 |
| 4,959,324 A | 9/1990 | Ramel et al. | 436/169 |
| 4,960,691 A | 10/1990 | Gordon et al. | 435/6 |
| 4,961,351 A | 10/1990 | Gerken | |
| 4,966,302 A | 10/1990 | Hjordie | |
| 4,973,549 A | 11/1990 | Khanna et al. | 435/11 |
| 4,981,786 A | 1/1991 | Dafforn et al. | 435/7 |
| 4,987,085 A | 1/1991 | Allen et al. | 436/169 |
| 5,002,198 A | 3/1991 | Smith | |
| 5,006,474 A | 4/1991 | Horstman et al. | 436/524 |
| 5,028,535 A | 7/1991 | Buechler et al. | 435/7.1 |
| 5,069,878 A | 12/1991 | Ehrenkranz | |
| 5,073,484 A | 12/1991 | Swanson et al. | 435/7.92 |
| 5,075,078 A | 12/1991 | Osikowicz et al. | 422/56 |
| 5,079,142 A | 1/1992 | Coleman et al. | 435/7.92 |
| 5,082,626 A | 1/1992 | Grage, Jr. | 422/56 |
| 5,085,988 A | 2/1992 | Olson | 435/7.91 |
| 5,089,391 A | 2/1992 | Buechler et al. | 435/7.1 |
| 5,092,478 A | 3/1992 | La Pierre | |
| 5,096,837 A | 3/1992 | Fan et al. | 436/514 |
| 5,111,947 A | 5/1992 | Patterson | |
| 5,115,934 A | 5/1992 | Nelson | |
| 5,116,576 A | 5/1992 | Stanley | 422/55 |
| 5,118,607 A | 6/1992 | Bignami et al. | 435/7.1 |
| 5,119,830 A | 6/1992 | Davis | 600/584 |
| 5,120,643 A | 6/1992 | Ching et al. | 435/7.92 |
| 5,135,199 A | 8/1992 | Cross et al. | |
| 5,141,850 A | 8/1992 | Cole et al. | 436/525 |
| 5,141,875 A | 8/1992 | Kelton et al. | 436/514 |
| 5,156,952 A | 10/1992 | Litman et al. | 435/7.91 |
| 5,165,572 A | 11/1992 | Bath | |
| 5,185,127 A | 2/1993 | Vonk | 422/56 |
| 5,186,367 A | 2/1993 | Hickerson | |
| 5,186,897 A | 2/1993 | Eason et al. | 422/100 |
| 5,202,268 A | 4/1993 | Kuhn et al. | 436/525 |
| 5,207,340 A | 5/1993 | Cochrane | |
| 5,232,835 A | 8/1993 | Litman et al. | 435/7.93 |
| 5,238,652 A | 8/1993 | Sun et al. | 422/61 |
| RE34,394 E | 9/1993 | Bunting | 436/500 |
| 5,252,496 A | 10/1993 | Kang et al. | 436/529 |
| D341,663 S | 11/1993 | Coulter | D24/225 |
| 5,260,193 A | 11/1993 | Olson | 435/7.91 |
| 5,266,497 A | 11/1993 | Imai et al. | 436/514 |
| 5,270,166 A | 12/1993 | Parsons et al. | 435/7.4 |
| 5,271,517 A | 12/1993 | Bowers | |
| 5,275,785 A | 1/1994 | May et al. | 422/56 |
| 5,279,330 A | 1/1994 | Debush | |
| 5,294,015 A | 3/1994 | Landis | |
| 5,296,347 A | 3/1994 | LaMotte, III | 435/5 |
| 5,308,775 A | 5/1994 | Donovan et al. | 436/518 |
| 5,354,692 A | 10/1994 | Yang et al. | 436/514 |
| 5,356,782 A | 10/1994 | Moorman et al. | 435/7.9 |
| 5,381,918 A | 1/1995 | Dahl | |
| 5,395,754 A | 3/1995 | Lambotte et al. | 435/607.4 |
| 5,399,486 A | 3/1995 | Cathey et al. | 435/7.9 |
| 5,403,551 A | 4/1995 | Galloway et al. | |
| 5,415,994 A | 5/1995 | Imrich et al. | 435/5 |
| 5,416,000 A | 5/1995 | Allen et al. | 435/7.92 |
| 5,424,193 A | 6/1995 | Pronovost et al. | 435/7.32 |
| 5,429,804 A | 7/1995 | Sayles | |
| 5,435,970 A | 7/1995 | Mamenta et al. | 422/56 |
| D361,842 S | 8/1995 | Nazareth et al. | D24/225 |
| 5,451,504 A | 9/1995 | Fitzpatrick et al. | 435/53 |

| | | | |
|---|---|---|---|
| D366,938 S | 2/1996 | Shartle et al. | D24/224 |
| 5,489,414 A | 2/1996 | Schreiber et al. | 422/64 |
| 5,500,350 A | 3/1996 | Baker et al. | 435/7.92 |
| 5,504,013 A | 4/1996 | Senior | 436/165 |
| D369,868 S | 5/1996 | Nazareth et al. | D24/225 |
| 5,523,051 A | 6/1996 | Gibson | 422/1 |
| 5,523,055 A | 6/1996 | Hansen et al. | |
| 5,591,645 A | 1/1997 | Rosenstein | 436/514 |
| 5,595,187 A | 1/1997 | Davis | |
| 5,597,532 A | 1/1997 | Connolly | 422/58 |
| 5,601,191 A | 2/1997 | Meandor | |
| 5,602,040 A | 2/1997 | May et al. | 436/514 |
| 5,622,871 A | 4/1997 | May et al. | 436/514 |
| 5,641,012 A | 6/1997 | Silversides | |
| 5,641,637 A | 6/1997 | Hudak et al. | 435/7.24 |
| 5,654,162 A | 8/1997 | Guire et al. | 435/7.92 |
| 5,656,503 A | 8/1997 | May et al. | |
| D384,971 S | 10/1997 | Kawan | D19/9 |
| 5,686,315 A | 11/1997 | Pronovost et al. | 436/510 |
| D388,167 S | 12/1997 | Caradonna et al. | D24/107 |
| 5,712,172 A | 1/1998 | Huang et al. | 436/518 |
| D390,667 S | 2/1998 | Nazareth | D24/223 |
| 5,714,389 A | 2/1998 | Charlton et al. | 436/514 |
| 5,716,778 A | 2/1998 | Weng et al. | 435/4 |
| 5,728,587 A | 3/1998 | Kang et al. | 436/518 |
| 5,739,041 A | 4/1998 | Nazareth et al. | 436/518 |
| D395,708 S | 6/1998 | Shartle et al. | D24/224 |
| 5,766,961 A | 6/1998 | Pawlak et al. | 436/510 |
| 5,770,460 A | 6/1998 | Pawlak et al. | 436/510 |
| 5,785,044 A | 7/1998 | Meandor et al. | |
| 5,807,752 A | 9/1998 | Brizgys et al. | 436/513 |
| 5,843,691 A | 12/1998 | Douglas et al. | 435/14 |
| 5,846,835 A | 12/1998 | Sisbarro et al. | 436/166 |
| D404,812 S | 1/1999 | Cipkowski | D24/107 |
| 5,869,006 A | 2/1999 | Fanning et al. | 422/67 |
| 5,874,216 A | 2/1999 | Mapes | 435/6 |
| 5,877,028 A | 3/1999 | Chandler et al. | 436/514 |
| 5,897,840 A | 4/1999 | Owens, Jr. et al. | |
| 5,904,898 A | 5/1999 | Markart | 422/61 |
| 5,916,815 A | 6/1999 | Lappe | 422/56 |
| 5,922,533 A | 7/1999 | Vallari et al. | 435/5 |
| 5,922,615 A | 7/1999 | Nowakowski et al. | 436/518 |
| 5,929,422 A | 7/1999 | Lappe | 235/462.13 |
| 5,932,430 A | 8/1999 | Larka et al. | 435/7.32 |
| 5,939,252 A | 8/1999 | Lennon et al. | 435/4 |
| 5,939,272 A | 8/1999 | Buechler et al. | 435/7.1 |
| 5,939,331 A | 8/1999 | Burd et al. | 436/518 |
| 5,962,333 A | 10/1999 | Incorvia et al. | 436/169 |
| 5,965,458 A | 10/1999 | Kouvonen et al. | 436/518 |
| 5,975,373 A | 11/1999 | Forsberg | |
| 5,976,469 A | 11/1999 | Davis | |
| 5,976,895 A | 11/1999 | Cipkowski | 422/102 |
| 5,981,293 A | 11/1999 | Charlton | 436/177 |
| 5,989,921 A | 11/1999 | Charlton et al. | 436/501 |
| 5,994,145 A | 11/1999 | Stave et al. | 436/139 |
| 6,008,056 A | 12/1999 | Thieme | 436/514 |
| D420,141 S | 2/2000 | Casterlin | D24/223 |
| 6,020,147 A | 2/2000 | Guire et al. | 435/7.92 |
| 6,025,203 A | 2/2000 | Vetter et al. | 436/170 |
| 6,087,184 A | 7/2000 | Magginetti et al. | 436/514 |
| D430,303 S | 8/2000 | Cipkowski | D24/225 |
| 6,096,563 A | 8/2000 | Hajizadeh et al. | 436/523 |
| 6,140,136 A | 10/2000 | Lee | 436/518 |
| D434,494 S | 11/2000 | Wilkinson et al. | D24/122 |
| 6,165,416 A | 12/2000 | Chandler | |
| 6,168,758 B1 | 1/2001 | Forsbert et al. | |
| 6,170,719 B1 | 1/2001 | Wilkinson et al. | |
| 6,171,261 B1 | 1/2001 | Niermann et al. | |
| 6,174,006 B1 | 1/2001 | Burt | |
| 6,187,269 B1 | 2/2001 | Lancesseur et al. | 422/61 |
| 6,187,598 B1 | 2/2001 | May et al. | 436/514 |
| 6,210,909 B1 | 4/2001 | Guirguis | |
| 6,228,660 B1 | 5/2001 | May et al. | 436/514 |
| 6,234,241 B1 | 5/2001 | Elmore | 165/122 |
| 6,248,598 B1 | 6/2001 | Bogema | 436/518 |
| 6,277,646 B1 | 8/2001 | Guirguis | |
| 6,284,195 B1* | 9/2001 | Lai et al. | 422/58 |
| D449,524 S | 10/2001 | Kieras | D9/430 |
| 6,306,642 B1 | 10/2001 | Nelson et al. | 435/287.1 |
| 6,308,848 B1 | 10/2001 | Parrinello | |
| 6,352,862 B1 | 3/2002 | Davis et al. | 436/510 |
| 6,372,515 B1 | 4/2002 | Casterlin et al. | 436/518 |
| 6,375,897 B1 | 4/2002 | Bachand | 422/58 |
| 6,379,620 B1 | 4/2002 | Tydings et al. | 422/58 |
| 6,382,444 B1 | 5/2002 | Nyman | |
| 6,403,383 B1 | 6/2002 | Casterlin | |
| 6,406,922 B2 | 6/2002 | Casterlin et al. | 436/518 |
| D464,141 S | 10/2002 | McMenamy et al. | D24/216 |
| 6,464,939 B1 | 10/2002 | Bachand | |
| 6,468,474 B2 | 10/2002 | Bachand | |
| D468,204 S | 1/2003 | Gittins et al. | D9/430 |
| D468,437 S | 1/2003 | McMenamy et al. | D24/216 |
| 6,565,808 B2* | 5/2003 | Hudak et al. | 422/58 |
| 6,576,193 B1* | 6/2003 | Cui et al. | 422/58 |
| 2002/0004019 A1 | 1/2002 | Bachand | |
| 2002/0023482 A1* | 2/2002 | Pampinella | 73/49.8 |
| 2002/0031845 A1 | 3/2002 | Cipkowski | |
| 2002/0046614 A1* | 4/2002 | Alley | 73/864.91 |
| 2002/0058031 A1 | 5/2002 | Tung et al. | 424/140.1 |
| 2002/0085953 A1 | 7/2002 | Parker | |
| 2002/0096469 A1* | 7/2002 | Faulkner | 210/464 |
| 2002/0137231 A1 | 9/2002 | Cipkowski | |
| 2002/0173047 A1 | 11/2002 | Hudak et al. | 436/178 |
| 2003/0004396 A1 | 1/2003 | Vanden Hock et al. | 600/37 |
| 2003/0022392 A1 | 1/2003 | Hudak | 436/518 |
| 2003/0027359 A1 | 2/2003 | Hudak et al. | 436/518 |
| 2003/0129767 A1 | 7/2003 | Bautista et al. | 436/178 |
| 2004/0053423 A1* | 3/2004 | LaBorde | 436/514 |

FOREIGN PATENT DOCUMENTS

| | | |
|---|---|---|
| EP | 0250137 B1 | 6/1987 |
| EP | 0183442 A2 | 3/1990 |
| EP | 0183442 B1 | 3/1990 |
| EP | 0291194 A1 | 2/1994 |
| EP | 0291194 B1 | 2/1994 |
| EP | 0284232 A1 | 10/2002 |
| EP | 0284232 B2 | 10/2002 |
| WO | 9733519 | 9/1997 |
| WO | WO98/38917 | 9/1998 |
| WO | WO 00/29111 | 5/2000 |
| WO | WO 00/62930 | 10/2000 |
| WO | 0095396 | 11/2002 |

OTHER PUBLICATIONS

"One step drug-of-abuse test," InTec Products, Inc. Product brochure, 2002.
ACON OEM Product brochure, Aug. 2000.
ACON magazine advertisement, IVD Technology Magazine, p. 45 Nov./Dec. 1999.
ACON magazine advertisement, IVD Technology Magazine, p. 17 Mar./Apr. 2000.
ACON magazine advertisement, LabMedica Magazine, Jul./Aug. p. 14; Sep./Oct. p. 9; Nov./Dec. p. 23; 1999.
www.3dl.net/drugtests.html., 4 pages (accessed on Nov. 9, 2001).
www.health.org/workplace/urinebook.html, 4 pages (accessed on May 2, 2001).

* cited by examiner (A)

(B)

(C)

(D)

(E)

(F)

SPECIMEN COLLECTION CONTAINER

TECHNICAL FIELD

The present invention relates generally to the field of sample collection and handling devices. This integrated sample collection and handling device can be used to manipulate samples, including samples used to test for analytes, in particularly drugs of abuse, antibodies, antigens and biological moieties such as glucose.

SUMMARY

Figure 1:
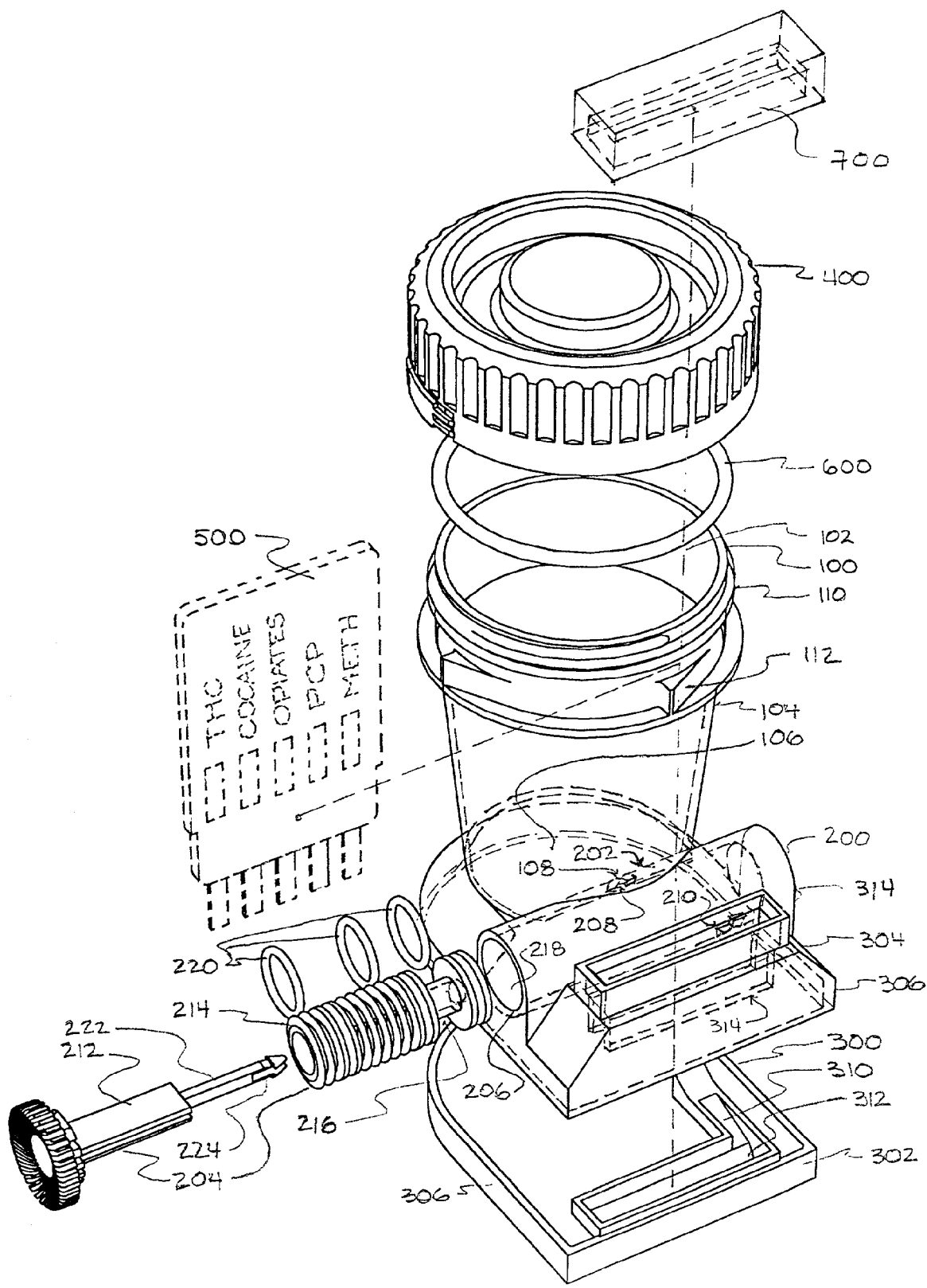
FIG. 1 depicts the relative spatial arrangement of the parts of the integrated sample collection and handling device and also the relative spatial alignment of a test device used with the device.

The present invention recognizes that sample collection and handling devices, particularly those used for testing for substances of abuse, do not allow for a separation of the bulk sample from a sample thereof to be tested. The present invention provides such a device and methods of use.

The present invention includes but is not limited to a specimen collection device that includes a chamber such that the chamber is capable of collecting a specimen. The device also includes a reservoir such that the reservoir is capable of receiving a portion of the specimen from the chamber and optionally so that the reservoir is capable of receiving a test device. The device optionally includes a valve functionally interposed between the chamber and the reservoir that is capable of transferring at least a portion of the specimen from the chamber to the reservoir such that the chamber and the reservoir are not in direct fluid communication. The device optionally includes a means for fluidic communication between the chamber, the valve and the reservoir.

The present invention also includes a method of detecting an analyte of interest in a specimen that includes providing a specimen collection device of the present invention; providing a specimen into the chamber; actuating the valve to transfer at least a portion of the specimen from the chamber to the reservoir; and contacting the transferred portion of the specimen within the reservoir with a test device.

The present invention includes a variety of other aspects. These aspects are detailed herein.

DETAILED DESCRIPTION OF THE INVENTION

Definition

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references.

Terms of orientation such as "up" and "down" or "upper" or "lower" and the like refer to orientation of the parts during use of the device. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings:

An element of the present invention is "integral to" another element of the present invention when the two elements are manufactured as a single piece.

An element of the present invention is "separate from" another element of the present invention when the two elements are manufactured as separate pieces.

"Directly" means that one structure is in physical contact with another structure, or, when used in reference to a procedure, means that one process effects another process or structure without the involvement of an intermediate step or component.

"Indirectly" means that one structure is not in immediate physical contact with another structure, but rather contacts an intermediary structure that contacts the other structure. When used in reference to a procedure, "indirectly" means that one process effects another process or structure by means of intermediate step or component.

A "reagent" can be any chemical, including organic compounds and inorganic compounds and combinations thereof. A reagent can be provided in gaseous, solid, or liquid form, or any combination thereof, and can be a component of a solution or a suspension. A reagent preferably includes fluids, such as buffers useful in methods of detecting analytes in a sample or specimen, such as anticoagulants, diluents, buffers, test reagents, specific binding members, detectable labels, enzymes and the like. A reagent can also include an extractant, such as a buffer or chemical, to extract an analyte from a sample or specimen or a sample collection device. For example, a buffer can be used to free biological components such as cells or etiological agents on or within a sample collection device, such as a swab. Alternatively, an extractant, such as an acid, can be use to extract analytes from the sample or specimen, such as LPS from bacteria.

A "barrier" is a thin piece of material that is not rigid. By "thin" it is meant that the thickness of the material is lesser that either its length or width. A "puncturable barrier" of the present invention can be punctured by a puncturing structure when brought into contact with a puncturable barrier with sufficient force, can protrude through a puncturable barrier. Suitable materials for barriers include foils, plastics, and foil-plastic laminates.

An "analysis device" or "test device" is a device for analyzing a sample or specimen. An analysis device can be used to detect the presence and/or concentration of an analyte in a sample or specimen, or to determine the presence and/or numbers of one or more components of a sample or specimen, or to make a qualitative assessment of a sample or specimen. Analysis devices of the present invention include, but are not limited to, cuvettes, slides, lateral flow detection devices such as test strip devices, and columns.

A "lateral flow detection device" is a device that determines the presence and/or amount of an analyte in a liquid sample or specimen as the liquid sample or specimen moves through a matrix or material by lateral flow, such as an immunochromatographic device.

"Sample application aperture" refers to the portion of an analysis device where an opening provides access to the portion of the analysis device that receives the sample or specimen. For example, a sample application aperture can provide access to a sample application zone of a test strip of a lateral flow detection device.

"Analyte" is the compound or composition to be measured that is capable of binding specifically to a ligand, receptor, or enzyme, usually an antibody or antigen such as a protein or drug, or a metabolite. The precise nature of antigenic and drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference. Analytes can include antibodies and receptors, including active fragments or fragments thereof. An analyte can include an analyte analogue, which is a derivative of an analyte, such as, for example, an analyte altered by chemical or biological methods, such as by the action of reactive chemicals, such as adulterants or enzymatic activity.

"Antibody" is an immunoglobulin, or derivative or fragment or active fragment thereof, having an area on the surface or in a cavity which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

"Sample" is any material to be tested for the presence and/or concentration of an analyte in a sample or specimen, or to determine the presence and/or numbers of one or more components of a sample or specimen, or to make a qualitative assessment of a sample or specimen. A sample can be the same as a specimen. Preferably, a sample is a fluid sample, preferably a liquid sample. Examples of liquid samples that may be tested using a test device of the present invention include bodily fluids including blood, serum, plasma, saliva, urine, ocular fluid, semen, and spinal fluid; water samples, such as samples of water from oceans, seas, lakes, rivers, and the like, or samples from home, municipal, or industrial water sources, runoff water or sewage samples; and food samples, such as milk or wine. Viscous liquid, semi-solid, or solid specimens may be used to create liquid solutions, eluates, suspensions, or extracts that can be samples. For example, throat or genital swabs may be suspended in a liquid solution to make a sample. Samples can include a combination of liquids, solids, gasses, or any combination thereof, as, for example a suspension of cells in a buffer or solution. Samples can comprise biological materials, such as cells, microbes, organelles, and biochemical complexes. Liquid samples can be made from solid, semi-solid or highly viscous materials, such as soils, fecal matter, tissues, organs, biological fluids or other samples that are not fluid in nature. For example, these solid or semi-solid samples can be mixed with an appropriate solution, such as a buffer, such as a diluent or extraction buffer. The sample can be macerated, frozen and thawed, or otherwise extracted to form a fluid sample. Residual particulates can be removed or reduced using conventional methods, such as filtration or centrifugation.

Other technical terms used herein have their ordinary meaning in the art that they are used, as exemplified by a variety of technical dictionaries.

Introduction

The present invention recognizes that sample handling devices, particularly those used for testing for substances of abuse, do not allow for a separation of the bulk sample from a sample thereof to be tested. The present invention provides such a device and methods of use.

As a non-limiting introduction to the breath of the present invention, the present invention includes several general and useful aspects, including but not limited to those set forth below.

1) A specimen collection device that includes a chamber, a reservoir and a valve such that the valve is functionally interposed between the chamber and the reservoir and is capable of transferring at least a portion of the specimen from the chamber to the reservoir such that the chamber and the reservoir are not in direct fluid communication.

2) A method of detecting an analyte of interest in a specimen that includes providing a specimen collection device of the present invention; providing a specimen into the chamber; actuating the valve to transfer at least a portion of the specimen from the chamber to the reservoir; and contacting the transferred portion of the specimen with a test device.

These enumerated aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention. In addition, a variety of other aspects and embodiments of the present invention are described herein.

I Specimen Collection and Handling Device

The present invention includes but is not limited to a specimen collection and handling device that includes a chamber 100 such that the chamber is capable of collecting a specimen. The device also includes a reservoir 300 such that the reservoir is capable of receiving a portion of the specimen from the chamber and optionally so that the reservoir is capable of receiving a test device 500. The device optionally includes a valve 200 functionally interposed between the chamber and the reservoir that is capable of transferring at least a portion of the specimen from the chamber to the reservoir such that the chamber and the reservoir are not in direct fluid communication.

Chamber

With reference to FIG. 1, the fact can be seen that the chamber 100 of the specimen collection device can take the form of any number of different symmetrical configurations such as cylindrical, convex, conical, elliptical, square, rectangular; unsymmetrical configurations such as peanut shaped, kidney shaped or hybrid combinations thereof all with an inner surface and an outer surface. Furthermore, the absolute size of the chamber 100 can be varied to meet the expected volumetric size of the specimen to be contained within the chamber 100.

The chamber 100 can have an upper opening 102 defined by the upper portion of the chamber 100 through which a specimen can be introduced into the interior of the chamber 100.

In one embodiment of the present invention the chamber 100 can have a side wall 104, a bottom wall 106 and a valve wall 202 with the chamber side wall 104 substantially tapered either outwardly from the top to the bottom of the side wall 104 or inwardly from the top to the bottom of the side wall 104. The chamber bottom wall 106 can take the form of a substantially flat wall forming the truncated portion of the inverted cone and the chamber valve wall 202 taking the form of a partially cylindrical shape which extends unitarily across an interior portion of both the chamber side wall 104 and chamber bottom wall 106. As will become increasing apparent from the following description of the invention, the position of the chamber valve wall 202 relative to the chamber side wall 104 and chamber bottom wall 106 can be varied and therefore influence the relative shape of the chamber valve wall 202. For example, the chamber valve wall 202 can be positioned so as to extend unitarily across only the chamber side wall 104 in an area just above the chamber bottom wall 106 so as to avoid contact with the chamber bottom wall 106. Alternatively, the chamber valve wall 202 can be positioned so as to extend unitarily across the chamber bottom wall 106 without touching the chamber side wall 104. In another variation of the present invention, the chamber valve wall 202 can take the shape of a cylinder passing through the interior of the chamber 100 and whose ends connect unitarily only with the chamber side wall 104. In even another variation, the valve 200 and reservoir can be arrayed on top of the chamber 100, preferably on a lid 400, which will permit a measured sampling of liquid and solid specimens once the specimen collection device is inverted or a measured sampling of gaseous specimens in any relative disposition of the specimen collection device.

Chamber 100 optionally includes a chamber orifice 108 communicatively connecting the inside and the outside of the chamber 100. In another embodiment, this same orifice communicatively connects the inside of the chamber 100 with the valve 200 as described below. In another alternative embodiment of the invention, the chamber orifice 108 is positioned in the upper portion of the chamber valve wall 202 equidistant from either end of the chamber valve wall 202. It is recognized the chamber orifice 108 can be gainfully positioned in any number of alternative locations. For example, if the chamber 100 is comprised of only one wall, the chamber orifice 108 can be positioned anywhere on the chamber wall or if the chamber 100 is comprised of two or more walls, anywhere on one of those chamber walls, be the wall a side wall 104, bottom wall 106 or valve wall 202.

Chamber 100 can optionally include a chamber seal 110 to facilitate the closure of the chamber upper opening 102. A non-exclusive list of mechanisms and methods that can be used to form seals useful in the present invention includes thermal welding, ultrasonic welding, vacuum sealing, compressive gaskets, screw-top lids, snap-top lids, compressive ring gaskets, gluing, compressive latch mechanisms, compressive spring mechanisms, snap couplings, bayonet couplings, zipping, hook and loop fasteners, screws, nails, bolting mechanisms, elastic band or bands, string and twine, wire, sliding mechanisms, plug or plugs, compressive clips, twist lids, epoxying, and tamper resistant mechanisms.

In another alternative embodiment of the present invention, there is included a tamper resistant seal or tamper evident seal to respectively prevent tampering with the chamber opening 102 or to facilitate the detection of tampering with the chamber upper opening 102. Tamper resistant seals can be of various types including a strap seal of the kind containing a series of ratchet teeth arranged along the strap, with one end of the strap being secured to the outer surface of the chamber 100 and the other end of the strap being lockably inserted into a lid hingeably attached to the upper end of the chamber 100 so as to move the ratchet teeth sequentially past a resiliently deformable catch in the lid as described in U.S. Pat. No. 6,174,006. Other suitable tamper resistant and tamper evident seals are found in the use of foil seals, tape seals, locks, glue, epoxy, hot wax seals which are well known in the art. Another tamper resistant or tamper evident seal is found in the use of a plastic heat shrunk band typically disposed around a sealed lid or plastic heat shrunk membrane typically disposed over a closure or opening. Attempted removal of or tampering with the closure causes the band to separate from the closure skirt, providing an indication of the tampering. Another method of providing a tamper resistant seal or tamper evident seal is to securely seal the present invention including the closed chamber 100 inside another container. A yet another method of providing a tamper resistant seal is found in the use of a lid 400 which irreversibly and unidirectionally engages with a series of sloped projections 112 arrayed around the outer wall of the upper outer portion of the chamber 100.

In a further alternative embodiment of the invention the chamber seal 110 can include a screw-lid 400. Such an embodiment can include an array of external threads unitary with and in proximity to the open top portion of the chamber side wall 104. The threads can rotatably mate with a similarly threaded lid 400 and thus hermetically seal the chamber 100 from outside contamination or adulteration and prevent the leakage or discharge of the contents of the chamber 100 during normal use conditions. In another embodiment of the present invention, the chamber seal 110 includes a snap-lid. Snap-on plastic hinged closures of the type mentioned above well known in the art and come in a large number of various designs. Conventional plastic snap-lid closures mainly include two basic elements. For one, they have a main joint around which the pivot movement of the lid in relation to the lower part takes place, and they furthermore have one or several intermediate elements creating the snap effect. Such intermediate elements can be in the form of straps, triangles or angled flexible springs or even longitudinally deformable tension spring elements. Snap-lid closures which can be incorporated into the present invention are found and described in the following U.S. Pat. Nos.: 3,688,942 September, 1972 Mitchell et al.; 4,165,018 August., 1979 Giggard; 4,177,930 December., 1979 Crisci; 4,421,244 December., 1983 Van Melle; 4,476,993 October., 1984 Krout; 4,718,571 January., 1988 Bordner; 4,966,302 October., 1990 Hjordie; 5,271,517 December., 1993 Bowers; 5,294,015 March., 1994 Landis; 5,381,918 January., 1995 Dahl; 2,280,31 May., 1880 Broughton; 4,249,82 April., 1890 Hidden; 3,837,518 September., 1974 Gach; 4,024,976 May., 1977 Acton; 4,111,329 September., 1978 Lampman; 4,190,175 February., 1980 Allen; 4,493,432 January., 1985 Smith; 4,512,493 April., 1985 Von Holdt; 4,646,926 March., 1987 Agbay et al.; 4,700,860 October., 1987 Li; 4,711,364 December., 1987 Letica; 4,718,571 January, 1988 Bordner; 4,807,771 February., 1989 Roy et al.; 4,886,184 December., 1989 Chamourian; 5,002,198 March., 1991 Smith; 5,092, 478 March., 1992 La Pierre; 5,111,947 May., 1992 Patterson; 5,115,934 May., 1992 Nelson; 5,207,340 May., 1993 Cochrane; 5,271,517 December., 1993 Bowers.

In one embodiment of the present invention, this chamber seal 110 is leak resistant. Such leak resistance can be provided by any of the variety of methods such as the sealing methods mentioned above.

In another embodiment of the present invention, the chamber seal 110 can contain at least one O-ring 600. Such O-rings are well known in the sealing arts and are commonly found in use in the food and cosmetic packaging industries. Suitable O-rings can be of the type commonly used in conjunction with cans and jars used in preserving fruit, vegetables and other food products, as well as pressure cookers, and other like containers used to maintain a pressure seal when closed. A conventional seal for ajar, which might be used in the present invention, includes a disk for covering the jar mouth and a ring for cinching the disk against the jar mouth. Similarly, the disk may be used to cover the upper chamber opening 102 and a ring for cinching the disk against the upper exterior portions of the chamber 100. An O-ring 600 is preferably provided generally disposed between the lid 400 and the edge of the chamber opening 102 so that pressure placed on the lid 400 during closure results in the tightening of the O-ring and assures a sealing contact. Representative patents describing suitable O-rings are found in U.S. Pat. No. 645,430 to Smelker, U.S. Pat. No. 711,452 to Meyer, British patent specification No. 485,051 to Fritsch, U.S. Pat. No. 2,967,944 to Davies, and U.S. Pat. No. 3,687,333 to Burnett et al.

O-rings of suitable composition include resilient elastomeric materials such as Nylon, Vinyl, Polyethylene, Polypropylene, Polyester, Epoxy, Polyolefins, silicone, fluoropolymers, polyurethanes or naturally occurring materials such as wax, cork, asbestos, rubber, chicle or metals such as copper, brass, steel, lead, tin and gold and their alloys.

In one embodiment of the present invention, the chamber seal 110 mentioned above is capable of resisting leakage when exposed to at least about half the standard sea level air pressure to at least about 100 pounds per square inch (PSI) internal pressure. In another embodiment of the present invention, the chamber seal 110 resists leakage when exposed to at least sea level air pressure to about 75 PSI internal pressure. In another alternative embodiment of the present invention, the chamber seal 110 mentioned above is capable of resisting leakage when exposed to at least about 25 to at least about 50 pounds PSI internal pressure. Other desirable ranges for the chamber seal 110 leakage resistance ranges can be between about 0.1 PSI and about 100 PSI, or about 1.0 PSI and about 99.9 PSI, or about 2.0 PSI and about 90 PSI, or about 3.0 PSI and about 80 PSI, or about 4.0 PSI and about 70 PSI, or about 5.0 PSI and about 60 PSI, or about 10 PSI and about 50 PSI. Optionally, the chamber seal 110 is capable of resisting leakage when exposed to pressures between about 0.1, 0.3, 0.5, 0.7, 0.9, 1, 3, 5, 7, 9, 10, 30, 50, 70, 90 or 100 PSI and about 0.2, 0.4, 0.6, 0.8, 2, 4, 6, 8, 20, 40, 60 or 80 PSI.

As mentioned above, the absolute size of the chamber 100 can be varied to meet or exceed the expected volumetric size of the specimen to be contained within the chamber 100. In particular, the chamber 100 size can be manufactured to accommodate specimen volumes of between about 0.00001 milliliter and about 1,000 milliliters. For the present invention, the volume of the chamber 100 can be between about 0.1 ml and about 1000 ml, or about 1.0 ml and about 999.9 ml, or about 10 ml and about 990 ml, or about 100 ml and about 900 ml, or about 200 ml and about 800 ml, or about 300 ml and about 700 ml, or about 400 ml and about 600 ml.

Optionally, the volume of the chamber 100 can be between about 0.00001, 0.00003, 0.00005, 0.00007, 0.00009, 0.0001, 0.0003, 0.0005, 0.0007, 0.0009, 0.0001, 0.0003, 0.0005, 0.0007, 0.0009, 0.001, 0.003, 0.005, 0.007, 0.009, 0.01, 0.03, 0.05, 0.07, 0.09, 0.1, 0.3, 0.5, 0.7, 0.9, 1, 3, 5, 7, 9, 10, 30, 50, 70, 90, 100, 300, 500, 700 or 900 ml and about 0.00002, 0.00004, 0.00006 0.00008, 0.0002, 0.0004, 0.0006 0.0008, 0.002, 0.004, 0.006 0.008, 0.02, 0.04, 0.06 0.08, 0.2, 0.4, 0.6, 0.8, 2, 4, 6, 8, 20, 40, 60, 80, 200, 400, 600, 800 or 1000 ml.

Another embodiment of the present invention can include the incorporation of a temperature sensing device with, on or inside the chamber 100 or within the chamber wall or walls. It is possible to use various types of temperature sensors, including liquid-in-glass thermometers, bimetallic sensors, thermocouples, resistance thermometers and thermistors. Silicon chip microcircuit technology offers another possible means for sensing temperature. Infra-red and other thermal imaging sensors can also be used to measure the temperature of the chamber 100 or the specimen contained within. Phase changing compounds such as crystals, waxes, paraffins, low temperature melting metals and metallic alloys also present themselves as possible means for sensing temperature in the present invention. In an alternative embodiment of the present invention, self-adhesive temperature-indicating labels such as those typically used in the drug testing field are affixed to a clear or transparent wall of the chamber 100.

It is also desirable, but not required, for there to be one or more labels or some other scribe-able or scribed surface or surfaces on the chamber 100 on which to print, write or display information. Such label or treated surface can be positioned on the outer wall of the chamber 100 and the printing, writing or display can be accomplished by gluing, imprinting, texturing, scribing, etching, surface treating, impregnating, painting, screen printing, dyeing, coloring, embossing, or other suitable method. Alternatively, such treatments can be applied to the interior of the chamber. In one embodiment of the present invention, a self-adhesive pre-printed label is affixed to the outer wall of the chamber 100. In another alternative embodiment of the present invention, this self-adhesive label can have a surface which accepts written notation through the use of a pen, pencil or marker or any such writing device.

The materials from which the chamber 100 can be manufactured are varied. The possible materials include metal, silicon, glass, ceramic, plastic and synthetic and natural polymers and combinations and mixtures thereof. In one embodiment of the present invention, the chamber 100 can be manufactured from a polypropylene composition using an appropriate manufacturing method such as pressure injection molding or machining. In another embodiment of the present invention the chamber 100 can be manufactured on a silicon chip or wafer using micro-machining techniques. With the use of other materials, there will necessarily be the need to utilize other suitable methods of manufacturing such as milling, casting, blowing, and spinning.

As mentioned previously, the chamber 100 can be of almost any conceivable shape which retains fluids. One alternative configuration for the chamber side wall 104 can be an outwardly sloping or tapered arrangement. Another alternative configuration for the chamber side wall 104 can be an inwardly sloping or tapered arrangement. The taper can range from about 1 to 50 degrees off perpendicular. A desirable angle for the chamber side wall 104 is between about 1 and 45 degrees off perpendicular. Even more desirable for the chamber side wall 104 angle are the tapers found between 1 and 35 degrees off perpendicular. One alternative embodiment of the present invention is to provide for a chamber side wall 104 taper of about 30 degrees off perpendicular. Other slopes for the chamber side wall 104 can be between about 0.1 degrees and about 50 degrees, or about 1.0 degree and about 49 degrees, or about 5.0 degrees and about 45 degrees, or about 1.0 degrees and about 40 degrees, or about 15 degrees and about 35 degrees, or about 20 degrees and about 30 degrees. Optionally, the slope for the chamber side wall 104 is between about 0.1, 0.3, 0.5, 0.7, 0.9, 1, 3, 5, 7, 9, 10, 30 or 50 degrees and about 0.2, 0.4, 0.6, 0.8, 2, 4, 6, 8, 20 or 40 degrees.

The specimen collection device can include the mating of the chamber 100 with or in close proximity to a test card or testing device. Hence, the chamber side wall 104 can be configured so as to accept the nearby positioning of the test card or test device 500. Various possibilities arise for the configuration of the chamber side wall 104 based upon the external shape of the test card or test device 500. If the test card or test device 500 has a circular, round or square shape, the chamber side wall 104 can then be configured to accept such various shapes. Most of present day test cards and test devices are substantially planar in configuration, thus, in an alternative embodiment of the present invention, along an external portion of the chamber side wall 104 of the present invention, there can be at least one substantially planar surface.

Reservoir

The specimen collection device can include at least one reservoir. The reservoir is configured to accept a measured portion of the specimen dispensed and delivered from the chamber 100 and to allow the testing of such measured portions of the specimen. In one embodiment of the reservoir, the reservoir includes a bottom part 302 and a top part 304. The top part 304 of the reservoir can be engaged to the lower portion of the chamber 100 while the bottom part 302 of the reservoir is separately arrayed. In another alternative embodiment of the present invention, the bottom part 302 of the reservoir can be engaged in a base unit 306 which engages the bottom portion of the chamber. In either alternative embodiment, the top part 304 of the reservoir is arrayed directly above the bottom part 302 of the reservoir in a functionally mated manner. The bottom part 302 of the reservoir can contain, but is not limited to containing, a sloping channel 310 which directs a measured portion of the specimen into a narrow trough 312 formed at the bottom of the sloping channel 310 which trough 312 is roughly equal in volume to the volume of measured portion of the specimen which is dispensed and delivered from the chamber 100 into the reservoir. It is in this trough 312 the measured portion of the specimen resides to be tested with a test device or element such as a test strip. As mentioned above, the top part 304 of the reservoir mates functionally with the bottom part 302 of the reservoir. In another alternative embodiment, the top part 304 of the reservoir can contain an opening 314 such as a slot to permit the functional engagement of a test strip or test device 500. In another alternative embodiment of the present invention, the top and bottom part 302 of the previously described reservoir are hermetically sealed together. In another embodiment of the reservoir, the opening 314 arrayed in the top part 304 of the reservoir is provided with a removable physical barrier. Suitable physical barriers can include, but are not limited to, plugs, films and self-adhesive seals made of paper, wax paper, plastic materials, thin metal films, metallicized plastic or paper, or a select scored cover made integral with the adjacent reservoir material at the top of the reservoir which scoring allows the selectively scored cover area to be removed through breakage of the scored areas.

In another embodiment of the present invention, a cover or seal 700 is arrayed over, on or in the top portion of the reservoir once the measured portion of the specimen is dispensed and delivered from the chamber 100 into the reservoir and the measured portion of the specimen has been tested. Such covering or sealing can similarly be accomplished by use of a number of the same physical barriers just described. Suitable physical barriers can include, but are not limited to, plugs, films and self-adhesive seals made of paper, wax paper, plastic materials, thin metal films, metallicized plastic or paper.

As with the chamber 100, the reservoir can be manufactured with various material. These materials can include metal, silicon, glass, ceramic, plastic and synthetic and natural polymers or any combination thereof. In one embodiment of the invention, the reservoir can be manufactured from a polypropylene composite using an appropriate manufacturing method such as pressure injection molding or machining. In another embodiment of the present invention the reservoir can be manufactured on a silicon chip or wafer using micro-machining techniques. Methods of manufacturing can include but are not limited to milling, casting, blowing, and spinning.

In one embodiment of the present invention, the reservoir will accept and engage either a test card or a test device 500 such as one or more test strips in a testably functional arrangement so as to permit the contact of the portion of the specimen with the appropriate sampling region or regions of the test card or test device 500. In an alternative embodiment of the present invention, this engagement is accomplished by configuring the opening 314 at the top portion of the reservoir to snugly engage the test device 500 such as through a slot. For example, the edges of a slot arrayed in the top part 304 of the reservoir may be lined with silicone or some other inert but flexible material which will snugly engage and allow insertion of the test device 500 through the slot. Alternatively the test card or test device 500 can be manufactured such that the reservoir slot and the test card or test device 500 can snap together through the use of interlocking lips and protrusions resulting in a snug fit. Another method which can be used to accomplish this same desired result can be accomplished by the use of self-adhesive tape or glue arrayed on the engaging surfaces of the either or both the reservoir slot or the test card or test device 500. In another embodiment of the present invention, the test card or test device 500 can be formed integral with the reservoir.

Specimen

The specimen collection device of the present invention is capable of collecting specimens including liquid specimens of the nature and character as described above in the definition portion of this disclosure. Alternatively, the specimen collection device can collect other types of specimens. For example, the specimen may be composed of fine powdery materials such as talc, carbon black, pharmaceutical preparations, or gases such as argon or methane. Additional specimens can include atmospheric specimens that can be tested for particulates or radioactive isotopes such as radon. The specimen collection device described herein would be useful for all such specimen types which require sample testing while all the while preserving an uncompromised portion of the original specimen for archiving and later analysis.

In an alternative embodiment of the present invention the specimen to be collected is a biological specimen. Such biological specimens include but are not limited to a sample from a subject such as an animal or a human. A sample from a subject can be of any appropriate type, such as a sample of fluid, tissue, organ or a combination thereof. The biological specimen can also be a sample of other biological material, such as food, including food such as material derived from plants or animals or combinations thereof. The sample can be processed prior to introduction into the chamber 100 or the chamber 100 can include reagents for use in such processing. In the alternative, a sample and reagent can be combined within the chamber 100. Such reagents can be used to process a sample, such as digesting solid samples with appropriate reagents such as chemicals, such as acids or bases, or with enzymes such as proteases. Other reagents can be used to extract analytes from a sample, such as extraction of antigens from biological entities, such as antigens from etiological agents such as bacteria, parasites, viruses or prions such as known in the art.

The specimen can also be an environmental sample, such as a sample of soil, water, wastewater, landfill or landfill leachate.

As mentioned above, the chamber 100 is expected to accommodate specimen volumes of between about 0.00001 milliliter and about 1,000 milliliters. For the present invention, the volume of the collected specimen can be between about 0.1 ml and about 1000 ml, or about 1.0 ml and about 999.9 ml, or about 10 ml and about 990 ml, or about 100 ml and about 900 ml, or about 200 ml and about 800 ml, or about 300 ml and about 700 ml, or about 400 ml and about 600 ml. Optionally, the volume of the specimen can be between about 0.00001, 0.00003, 0.00005, 0.00007, 0.00009, 0.0001, 0.0003, 0.0005, 0.0007, 0.0009, 0.0001, 0.0003, 0.0005, 0.0007, 0.0009, 0.001, 0.003, 0.005, 0.007, 0.009, 0.01, 0.03, 0.05, 0.07, 0.09, 0.1, 0.3, 0.5, 0.7, 0.9, 1, 3, 5, 7, 9, 10, 30, 50, 70, 90, 100, 300, 500, 700 or 900 ml and about 0.00002, 0.00004, 0.00006 0.00008, 0.0002, 0.0004, 0.0006 0.0008, 0.002, 0.004, 0.006, 0.008, 0.02, 0.04, 0.06 0.08, 0.2, 0.4, 0.6, 0.8, 2, 4, 6, 8, 20, 40, 60, 80, 200, 400, 600, 800 or 1000 ml.

While a number of different biological specimens are suitable for collection by the present invention, commonly collected specimens are biological samples, including but not limited to fluid sample including urine, blood, serum, saliva, semen, secretions including vaginal secretions, central nervous system fluids, ravages and the like.

Valve

Another aspect of the specimen collection device can include at least one valve 200. While in the first functional mode the valve 200 functions so as acquire a measured portion of a specimen from the specimen collected in the chamber 100 of the specimen collection device while at the same time sealing off and protecting the chamber 100 interior, specimen, valve interior and measured portion of the specimen from contaminating agents in the surrounding environment. During the second functional mode the valve 200 physically separates the measured portion of the specimen from the specimen remaining in the chamber 100 while continuing to seal off and protect the chamber 100 interior, specimen, valve interior and measured portion of the specimen from contaminating agents in the surrounding environment. While in these first two functional modes the valve 200 also acts to prevent the leakage of the specimen from the chamber 100 and the measured portion of the specimen from the valve 200. The third function of the valve 200 is to deliver and dispense the measured portion of the specimen into the reservoir while continuing to seal off and protect the chamber 100 interior and specimen from contaminating agents in the surrounding environment. Throughout this last functional mode, the valve 200 acts to prevent the leakage of the specimen from chamber 100.

As is evident by the above disclosure and by reference to the figures provided herewith, the valve 200 can take any number of different configurations. The valve 200 can be a tube with a substantially oval cross section when viewed on end. Alternatively, the valve 200 can be rectangular with a substantially square or rectangular cross section when viewed on end. In one embodiment of the present invention, however, the valve 200 is substantially cylindrical.

There are alternative means for accomplishing the three functional modes described above for the valve 200 of the present invention. One such means is to use a collapsible tube to acquire a measured portion of the specimen from the specimen collected in the chamber 100 of the specimen collection device. One end of the tube is in fluidic communication with the chamber orifice 108 while the other end of the valve tube can be temporarily maintained under a pressure releaseable seal. After transfer of a measured portion of the specimen from the chamber 100 into the valve 200, a crimp can be applied to the tube to physically separate the measured portion of the specimen from the specimen remaining in the chamber 100. This crimping acts to further seal off and protect the chamber 100 interior, specimen, tube interior and measured portion of the specimen from contaminating agents in the surrounding environment. While in these first two functional modes of collecting and crimping, the tube also can prevent leakage of the specimen from the chamber 100 and the measured portion of the specimen from the tube. Finally, an external force can be applied to the tube so as to create sufficient pressure within the tube to rupture or break the sealed end of the tube and release the measured portion of the specimen from the tube and into the specimen collection device reservoir. This embodiment of the present invention can deliver and dispense the measured portion of the specimen into the reservoir while maintaining a seal to protect the chamber 100 interior and remaining specimen from contaminating agents in the surrounding environment. Throughout this last functional mode, the tube also continues to prevent the leakage of the specimen from chamber 100.

In one alternative embodiment for the present invention the valve 200 includes a valve piston 204 configuration arrayed slidably within a substantially cylindrical valve body 206.

In another embodiment of the present invention, the valve 200 can move in only one direction and is thus unidirectional. One method of providing unidirectional motion of the valve 200 can include providing a valve piston 204 with two different movable sections slidably arrayed in a linear fashion within a cylindrical valve body 206. The valve body 206 can contain a first valve orifice 208 in fluidic communication with the chamber orifice 108 and can also contain a second orifice 210 in fluidic communication with the reservoir of the specimen collection device. In one embodiment of the present invention the valve piston 204 includes at least two slideably moving sections. The first section of the valve piston 204 is a handle 212 and the second section is a plunger 214 which contains a means 216 for acquiring the measured portion of the specimen from the specimen. Prior to use the valve handle 212 and plunger 214 are arrayed in a slidably engaged and actuated manner inside the valve body 206 such that the acquisition means 216 is in fluidic communication with the chamber 100 of the specimen collection device through the chamber orifice 108 and can acquire a measured portion of the specimen from the specimen collected in the chamber 100. A measured portion of the specimen in the chamber 100 is acquired and collected in the valve plunger 214. The valve handle 212 is slid into physical contact with the valve plunger 214 through the application of sufficient slideable force to the valve handle 212. The slideable force is maintained and the valve handle 212 engages and slides the valve plunger 214 to a position in the valve body 206 where the acquisition means 216 is no longer in fluidic communication with the chamber 100. The acquisition means 216 can then deliver and dispense the measured portion of the specimen into the reservoir through the second valve body orifice 210. The handle 212 may be slidably retracted from the valve plunger 214 and returned to substantially the valve handle's original position. In this alternative embodiment the valve plunger 214 is no longer in engaging contact with the valve handle 212 and is thus limited to unidirectional motion.

An alternative embodiment for engaging the valve handle 212 to the valve plunger 214 is to utilize a screw mechanism arrayed in a twistingly actuated fashion between the valve handle 212 and the valve body 206 such that twisting the valve handle 212 forces the valve handle 212 engage the valve plunger 214 such that the valve plunger 214 can be pushed or slid along the valve body 206.

In another embodiment of the present invention, the means 216 for transferring a portion of the specimen in the valve 200 cannot be slidably reversed or actuated more than once. Valves can be made unidirectional in a number of different ways. One method is through the use of a ratcheting mechanisms such as described in U.S. Pat. No. 6,174,006. A means of assuring that the valve 200 cannot be slidably actuated more than once can include the utilization of the two part valve assembly previously described since after actuation, the valve handle 212 functionally disengages from the valve plunger 214 and cannot then slidably force the plunger 214 to move in the reverse direction.

In another embodiment, the valve 200 of the present invention contains a valve seal 218. One type of suitable seal for the valve 200 can be created by lining substantially the complete interior of the cylindrical valve body 206 with a resilient film such as a silicone polymer. Other suitable seals for the valve 200 include those typically encountered in manual or powered syringes used for injecting a fluid into a patient. Such syringes typically include a reciprocally slidable plunger disposed within a cylindrical syringe body. A number of injector-actuated syringes and powered injectors for use in angiography, computed tomography and NMR/MRI have been developed. In general, syringe plungers for use with such powered injectors require an elastomeric cover which forms a sealing engagement with the inner wall of the syringe barrel. To reduce friction and provide an adequate seal, the syringe barrel, the plunger and the elastomeric plunger cover are typically lubricated during manufacture with, for example, a silicone oil lubricant. U.S. Pat. Nos. 4,628,969 and 4,718,463 describe such lubrication.

In one embodiment of the present invention the valve 200 can include at least one resilient O-ring 220 in sealing contact with the inner diameter of the valve body 206. The O-ring 220 can be in sealing engagement with the inner wall of the cylindrical valve body 206. The 0ring 220 can be alternatively seated in a seating formed around the circumference of the body of the valve plunger 214. The seating includes a ramp portion having a forward radius that is smaller than a rearward radius thereof. The ramp portion thus extends radially outward toward the rear thereof. As the valve plunger 214 is moved forward, frictional contact with the inner wall of the cylindrical valve body 206 and increasing fluid pressure of the measured portion of the specimen force the O-ring 220 to move rearward along the ramp portion of the seating. The increasing radius of the ramp portion causes the O-ring 220 to exert greater force upon the inner wall of the cylindrical valve body 206, thereby ensuring a substantially sealing engagement between the O-ring 220 and the inner wall of the valve body 206. In another alternative embodiment of the present invention, multiple O-ring 220s can be arrayed in a spaced circumferential manner around the valve plunger 214. O-ring 220s of suitable composition include resilient elastomeric materials such as Nylon, Vinyl, Polyethylene, Polypropylene, Polyester, Epoxy, Polyolefins, silicone, fluoropolymers, polyurethanes or naturally occurring materials such as wax, cork, asbestos, rubber, chicle or metals such as copper, brass, steel, lead, tin and gold and their alloys.

Figure 2:
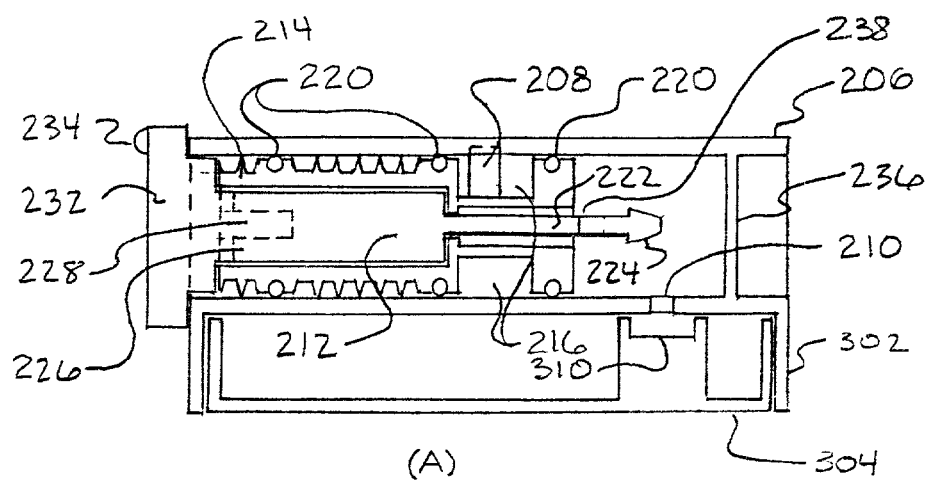
FIGS. 2A-F present the valve 200 in a series of longitudinal cross sections which show the arrangement and stepwise action of the valve components.
Figure 2:
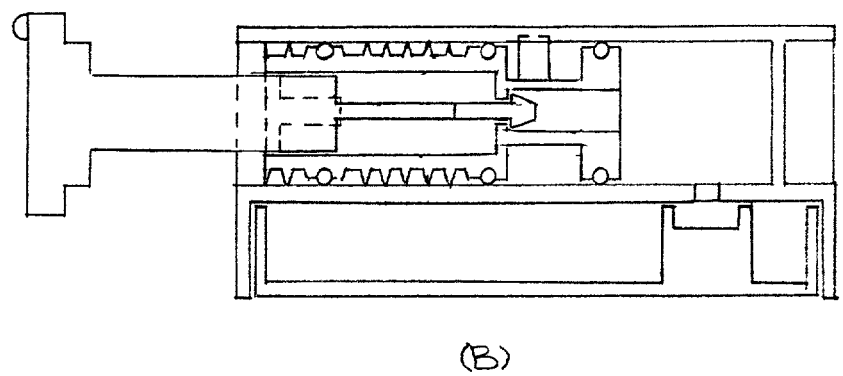
Figure 2:
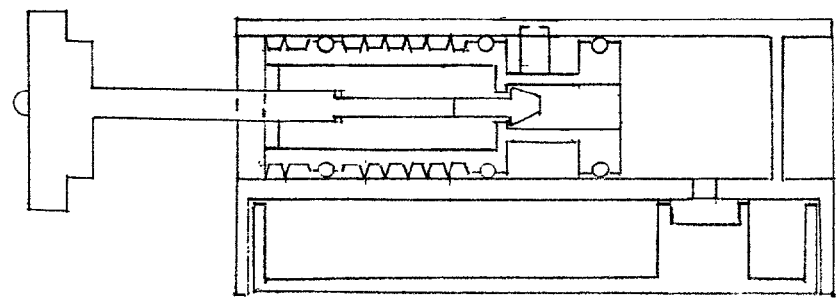
Figure 2:
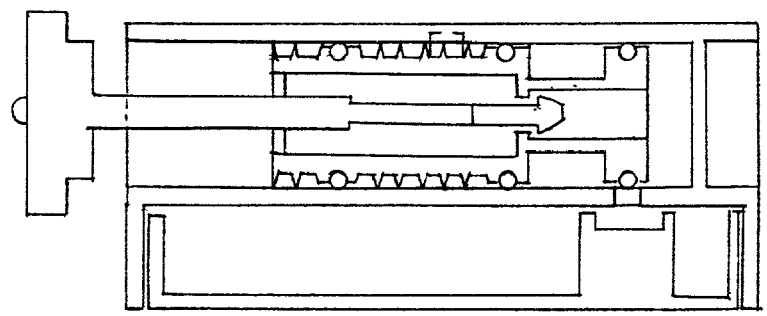
Figure 2:
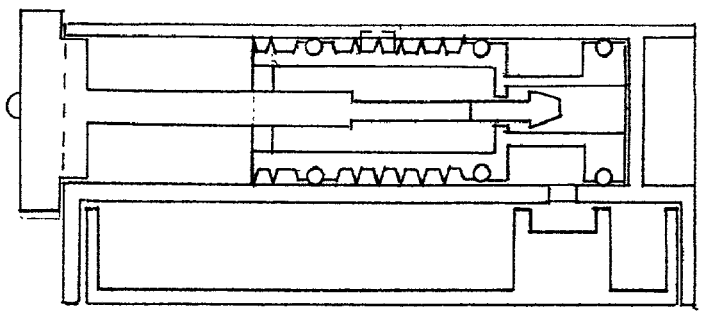
Figure 2:
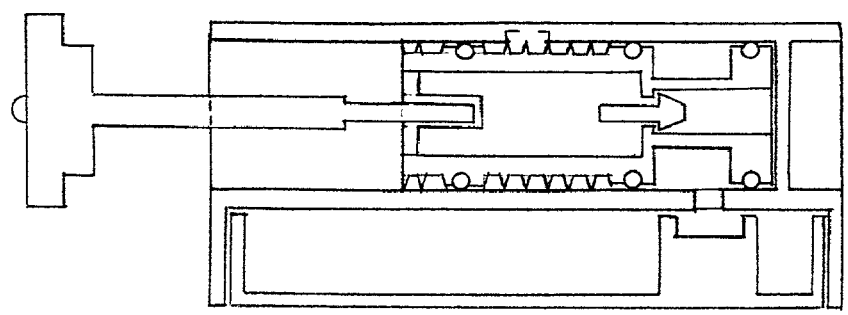
Figure 3:
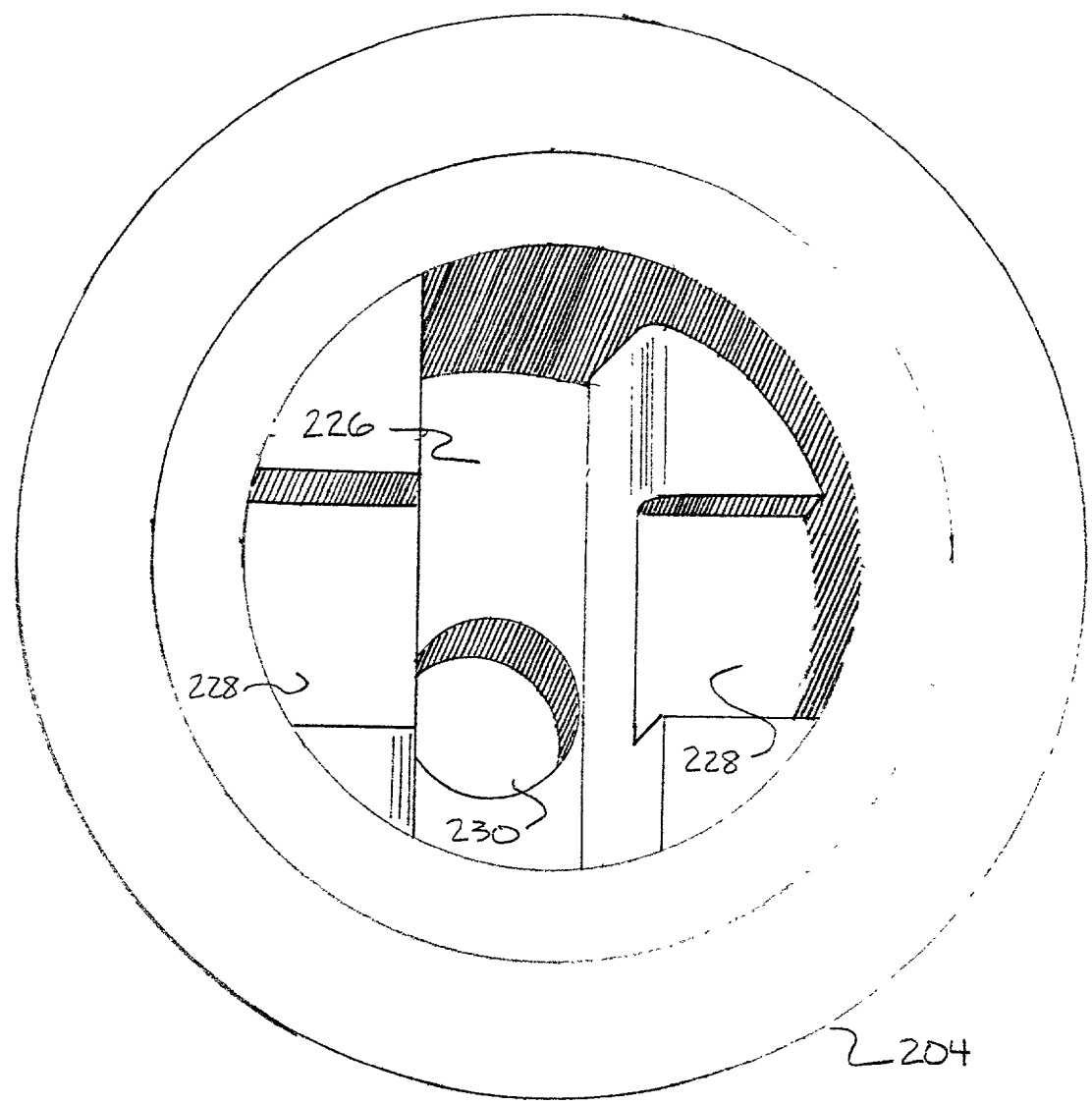
FIG. 3 shows in enlarged detail the interior of the valve piston 204 as viewed on end.

FIGS. 2 and 3 show another embodiment of the valve 200. FIG. 2 presents the valve 200 in a series of longitudinal cross sections which shows the arrangement and stepwise action of the valve components while FIG. 3 shows in enlarged detail the interior of the valve piston 204 as viewed on end. FIG. 2(A) shows the valve handle 212 with its guiding pin 222 and detachable head 224 arrayed in the valve piston 204 in the initial shipping position. When arrayed in this initial shipping position the valve handle knob 232 touches the end of cylindrical valve body 206 and the knob location indicator 234 is in the upper most position. In this initial shipping position it can be seen that the valve handle 212 is arrayed in an upright fashion inside of the vertical key slot 226 of the valve piston 204. FIG. 2(B) shows the valve handle 212 with its guiding pin 222 and detachable head 224 partially slideably withdrawn from valve piston 204 such that the valve handle 212 clears the vertical key slot 226 of the valve piston 204. As FIG. 2(B) also shows, the valve handle detachable head 224 is too wide to pass through the piston central orifice 230 and so provides a tactile clue that the valve handle 212 has indeed been withdrawn far enough to clear the vertical key slot 226 of the valve piston 204. FIG. 2(C) shows the one quarter clockwise rotation of the valve handle 212 to a horizontal position so that the valve handle 212 is engaged with the horizontal key slots 228 of the valve piston 204. FIG. 2(D) shows the displacement of the valve piston 204 part way across the cylindrical valve body 206. This motion is caused by the application of a force to the valve handle knob 232 sufficient to cause the attached valve handle 212 to engage with the horizontal key slots 228 of the valve piston 204 and to move the valve piston in a slideable fashion. FIG. 2(E) shows the valve handle 212 with its guiding pin 222 and detachable head 224 arrayed in the valve piston 204 in the final dispensing position. This position is reached when the valve handle knob 232 again touches the end of cylindrical valve body 206. In this final dispensing position, the valve piston 204 is stopped by the valve end wall 236. FIG. 2(F) shows the separation of the detachable head 224 from the valve handle guiding pin 222 upon an attempted removal or repositioning of the valve piston 204. The separation takes place at a fragile connection 238 located between the detachable head 224 and the guiding pin 222.

Another alternative aspect of the valve 200 is for the valve 200 to resists the leakage of specimen and outside contaminants between the chamber 100 and the reservoir. As mentioned above, one embodiment of the present invention can provide such assurance through the use of one or more O-ring 220s or by lining substantially the complete interior of the cylindrical valve body 206 with a resilient film such as a silicone polymer.

In one embodiment, the valve 200 of the present invention is capable of resisting leakage when exposed to at least about half the standard sea level air pressure to at least about 100 pounds per square inch (PSI) internal pressure. In another embodiment of the present invention, the valve 200 resists leakage when exposed to at least seal level air pressure to about 75 PSI internal pressure. In another embodiment of the present invention, the valve 200 mentioned above is capable of resisting leakage when exposed to at least about 25 to at least about 50 pounds PSI internal pressure. Other desirable ranges for the valve 200 leakage resistance ranges can be between about 0.1 PSI and about 100 PSI, or about 1.0 PSI and about 99.9 PSI, or about 2.0 PSI and about 90 PSI, or about 3.0 PSI and about 80 PSI, or about 4.0 PSI and about 70 PSI, or about 5.0 PSI and about 60 PSI, or about 10 PSI and about 50 PSI. Optionally, the valve 200 is capable of resisting leakage when exposed to pressures between about 0.1, 0.3, 0.5, 0.7, 0.9, 1, 3, 5, 7, 9, 10, 30, 50, 70, 90 or 100 PSI and about 0.2, 0.4, 0.6, 0.8, 2, 4, 6, 8, 20, 40, 60 or 80 PSI.

The valve 200 can be manufactured with various materials. Materials can include metal, silicon, glass, ceramic, plastic and synthetic and natural polymers or any combination thereof. In one embodiment of the present invention, the valve 200 is manufactured from a polypropylene composition using an appropriate manufacturing method such as pressure injection molding or machining. In another embodiment of the present invention the valve 200 can be manufactured on a silicon chip or wafer using micromachining techniques. Methods of manufacturing can include but are not limited to milling, casting, blowing, and spinning.

Chamber, Reservoir and Valve Configurations

As should be apparent from the above disclosure and the drawings, the chamber 100 and reservoir 300 can be constructed in a number of different arrangement. In one embodiment of the present invention, however, the chamber 100 and reservoir 300 form a single unit.

In another embodiment of the present invention, the chamber 100 and reservoir form separate units.

As a refinement of the present invention, the reservoir 300 is attachable with and is attached to the separate chamber 100. Suitable means of attaching include thermal welding, ultrasonic welding, vacuum sealing, compressing gaskets, screw mechanisms, snap couplings, gluing, compressive latching mechanisms, compressive spring mechanisms, bayonet couplings, zipping, hook and loop fasteners, screws, nails, bolting mechanisms, elastic band or bands, string and twine, wire, sliding mechanisms, compressive clips, and epoxying.

As even a further refinement of the present invention, the reservoir 300 is designed to be removable from the chamber 100. Suitable means of ensuring removability include the use of thermowelding, ultrasonic welding, vacuum sealing, compressing gaskets, screw mechanisms, snap couplings, gluing, compressive latching mechanisms, compressive spring mechanisms, bayonet couplings, zipping, hook and loop fasteners, screws, nails, bolting mechanisms, elastic band or bands, string and twine, wire, sliding mechanisms, compressive clips, and epoxying.

Test Device

The test device 500 of the present invention can be of any test element known in the art and preferably comprises at least one lateral flow detection device such as a test strip. (For examples of test devices and test strips see U.S. patent applications Ser. No. 09/579672; 09/579673; 09/653032; 60/233739 and 09/860408). The one or more test strips can be of any shape and dimensions, but preferably is a rectangular test strip. The one or more test strips can be used separately or can be arrayed on or in a common support such as a test card. Preferably, multiple test strips of a test device 500 can be arranged such that the sample application regions of the test strips can be contacted with the specimen in the reservoir 300 of the present invention.

The test strip of a test device 500 of the present invention may comprise, at least in part, any bibulous or non-bibulous material, such as nylon, paper, glass fiber, dacron, polyester, nitrocellulose, polyethylene, olefin, or other thermoplastic materials such as polyvinyl chloride, polyvinyl acetate, copolymers of vinyl acetate and vinyl chloride, polyamide, polycarbonate, polystyrene, etc. In a preferred embodiment, at least one test strip material is nitrocellulose having a pore size of at least about 1 micron, more preferably of greater than about 5 microns, or about 8-12 microns. Very suitable nitrocellulose sheets having a nominal pore size of up to approximately 12 microns, are available commercially from, for example, Schleicher and Schuell GmbII.

A test strip can include one or more materials. If a test strip comprises more than one material, the one or more materials are preferably in fluid communication with the measured portion of the specimen. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and may or may not partially overlap one another.

The material or materials of the test strip can be bound to a support or solid surface such as found, for example, in thin-layer chromatography and may have an absorbent pad either as an integral part or in liquid contact. For example, a test strip may comprise nitrocellulose sheet "backed", for example with a supporting sheet, such as a plastic sheet, to increase its handling strength. This can be manufactured by forming a thin layer of nitrocellulose on a sheet of backing material. The actual pore size of the nitrocellulose when backed in this manner will tend to be lower than that of the corresponding unbacked material. Alternatively, a preformed sheet of nitrocellulose and/or one or more other bibulous or non-bibulous materials can be attached to at least one supporting sheet, such as a sheet made of polymers (see, U.S. Pat. No. 5,656,503 to May et al., issued Aug. 12, 1997). The supporting sheet can be transparent, translucent or opaque. In the aspect of the present invention where the support sheet is transparent, the supporting sheet is preferably moisture impervious but can be moisture resistant or moisture pervious. The test strip can be assembled in a test device 500 such that the support sheet is optionally on the side of the test strip that can be viewed from the upper face of the test device 500. In this way the one or more test strips can be viewed along the surface of a test device 500 or through openings in a test device 500 housing the one or more test strips. In another embodiment of the present invention the one or more test strips can be viewed through a window comprised of a transparent material such as glass, plastic, or mylar, but preferably break resistant.

In the following discussion strips of test strip material will be described by way of illustration and not limitation.

Generally, test strips of a test device 500 of the present invention include a sample application zone and a test results determination region. The test results determination region can include either or both of one or more analyte detection zones and one or more control zones. Optionally, a test strip can include a reagent zone.

One or more specific binding members in the test results determination region of the test strip can be impregnated throughout the thickness of the bibulous or non-bibulous material in the test results determination region (for example, specific binding members for one or more analytes can be impregnated throughout the thickness of the test strip material in one or more analyte detection zones, and specific binding members for one or more control analytes can be impregnated throughout the thickness of the test strip material in one or more control zones, but that need not be the case). Such impregnation can enhance the extent to which the immobilized reagent can capture an analyte present in the migrating sample or specimen. Alternatively, reagents, including specific binding members and components of signal producing systems may be applied to the surface of the bibulous or non-bibulous material. Impregnation of specific binding members into test strip materials or application of specific binding members onto test strip materials may be done manually or by machine.

Nitrocellulose has the advantage that a specific binding member in the test results determination zone can be immobilized without prior chemical treatment. If the porous solid phase material comprises paper, for example, the immobilization of the antibody in the test results determination zone can be performed by chemical coupling using, for example, CNBr, carbonyldiimidazole, or tresyl chloride.

Following the application of a specific binding member to the test results determination zone, the remainder of the porous solid phase material may be treated to block any remaining binding sites elsewhere. Blocking can be achieved by treatment with protein (for example bovine serum albumin or milk protein), or with polyvinylalcohol or ethanolamine, or any combination of these agents. A labeled reagent for the reagent zone can then be dispensed onto the dry carrier and will become mobile in the carrier when in the moist state. Between each of these various process steps (sensitization, application of unlabeled reagent, blocking and application of labeled reagent), the porous solid phase material should be dried.

To assist the free mobility of the labeled reagent when the test strip is moistened with the sample or specimen, the labeled reagent can be applied to the bibulous or non-bibulous material as a surface layer, rather than being impregnated in the thickness of the bibulous material. This can minimize interaction between the bibulous or non-bibulous material and the labeled reagent. For example, the bibulous or non-bibulous material can be pre-treated with a glazing material in the region to which the labeled reagent is to be applied. Glazing can be achieved, for example, by depositing an aqueous sugar or cellulose solution, for example of sucrose or lactose, on the carrier at the relevant portion, and drying (see, U.S. Pat. No. 5,656,503 to May et al., issued Aug. 12, 1997). The labeled reagent can then be applied to the glazed portion. The remainder of the carrier material should not be glazed.

The reagents can be applied to the carrier material in a variety of ways. Various "printing" techniques have previously been proposed for application of liquid reagents to carriers, for example micro-syringes, pens using metered pumps, direct printing and ink-jet printing, and any of these techniques can be used in the present context. To facilitate manufacture, the carrier (for example sheet) can be treated with the reagents and then subdivided into smaller portions (for example small narrow strips each embodying the required reagent-containing zones) to provide a plurality of identical carrier units.

In embodiments where the analyte is detected by a signal producing system, such as by one or more enzymes that specifically react with the analyte, one or more components of the signal producing system can be bound to the analyte detection zone of the test strip material in the same manner as specific binding members are bound to the test strip material, as described above. Alternatively or in addition, components of the signal producing system that are included in the sample application zone, the reagent zone, or the analyte detection zone of the test strip, or that are included throughout the test strip, may be impregnated into one or more materials of the test strip. This can be achieved either by surface application of solutions of such components or by immersion of the one or more test strip materials into solutions of such components. Following one or more applications or one or more immersions, the test strip material is dried. Alternatively or in addition, components of the signal producing system that are included in the sample application zone, the reagent zone, or the analyte detection zone of the test strip, or that are included throughout the test strip, may be applied to the surface of one or more test strip materials of the test strip as was described for labeled reagents.

Sample Application Zone

The sample application zone is an area of a test strip where a sample, such as a fluid sample, such as a biological fluid sample such as blood, serum, saliva, or urine, or a fluid derived from a biological sample, such as a throat or genital swab, is applied. The sample application zone can include a bibulous or non-bibulous material, such as filter paper, nitrocellulose, glass fibers, polyester or other appropriate materials. One or more materials of the sample application zone may perform a filtering function, such that large particles or cells are prevented from moving through the test strip. The sample application zone can be in direct or indirect fluid communication with the remainder of the test strip, including the test results determination zone. The direct or indirect fluid communication can be, for example, end-to-end communication, overlap communication, or overlap or end-to-end communication that involves another element, such as a fluid communication structure such as filter paper such as disclosed and depicted in U.S. patent application Ser. No. 09/860408.

The sample application zone can also include compounds or molecules that may be necessary or desirable for optimal performance of the test, for example, buffers, stabilizers, surfactants, salts, reducing agents, or enzymes.

Reagent Zone

The test strip can also include a reagent zone where reagents useful in the detection of an analyte can be provided immobilized (covalent or non-covalent immobilization) or not immobilized, particularly when in a fluid state. The reagent zone can be on a reagent pad, a separate segment of bibulous or non-bibulous material included on the test strip, or it can be a region of a bibulous or non-bibulous material of a test strip that also includes other zones, such as an analyte detection zone. In one aspect of the invention, the reagent zone can include a labeled specific binding member, such as antibodies or active fragments thereof attached or linked to a label. Such labeled specific binding members can be made using methods known in the art. The specific binding members can bind an analyte and/or can bind a control compound.

In one preferred example involving detection of hCG, the reagent zone includes two populations of colored beads. One population of colored beads is attached to an anti-rabbit IgG antibody or active fragment thereof and the other population of colored beads is attached to an anti-hCG beta chain antibody or active fragment thereof. The labeled anti-rabbit IgG antibody or antibody fragment is used for visual detection of a signal in the control zone of the test strip. A color signal in the control zone indicated that the sample has passed through the detection zone. The labeled anti-hCG beta chain antibody or fragment thereof provides a visual signal in the detection zone indicating the presence of hCG in the sample.

Other preferred embodiments are having anti-(drug of abuse) antibodies or active fragments thereof bound to a population of colored beads. More than one population of beads can be used as in the forgoing example to provide a visual signal in the detection zone and a second visual signal in the control zone. The two populations of beads can be the same or different colors or be provided as a mixture of colors. Alternatively or in addition, different populations of beads bound to different antibodies or antibody fragments can be used to indicate the presence of more than one analyte in a sample by producing one or more visual signals in one or more detection zones.

In another aspect of the invention, the reagent zone includes the analyte or an analyte analog bound to a population of colored beads. In this case, the analyte in the sample competes with the labeled analyte or analyte analog provided in the reagent zone for binding to a specific binding member in the test results determination zone. A reduced visual signal in comparison with a control sample lacking analyte indicates the presence of analyte in the sample. More than one population of beads can be used as in the forgoing examples to provide a visual signal in the analyte detection zone and a second visual signal in the control zone. Alternatively or in addition, different populations of beads bound to different analytes or analyte analogs can be used to indicate the presence of more than one analyte in a sample by producing one or more visual signals in one or more detection zones.

Preferred labels are beads such as metal particles, such as gold, or polymeric beads, such as colored beads, or particles of carbon black. Other labels include, for example, enzymes, chromophores or fluorophores such as they are known in the art, particularly in immunoassays, or later developed. The populations of beads are provided in powdered form on the reagent zone, which can include a bibulous material, such as filter paper, glass fibers, nylon, or nitrocellulose. These reagents are reversibly bound to the reagent zone because they can be mobilized when placed in contact with a fluid, such as a fluid sample passing along a test strip.

In another embodiment of the invention, the reagent zone can include components of a signal producing system, for example, catalysts, such as enzymes, cofactors, electron donors or acceptors, and/or indicator compounds.

The reagent zone can also include compounds or molecules that may be necessary or desirable for optimal performance of the test, for example, buffers, stabilizers, surfactants, salts, reducing agents, or enzymes.

A Test Results Determination Zone

The test results determination zone includes immobilized or not immobilized reagents that can detect the presence of the analyte being tested for, such as but not limited to, drugs of abuse, hormones, metabolites, and antibodies. Such reagents are preferably in a dry state and can be covalently immobilized, non-covalently immobilized, or not immobilized in a fluid state. The test result determination zone can include either or both of one or more analyte detection zones and one or more control zones.

Depending on the particular format and analyte being tested for, a variety of reagents can be provided at the test results determination zone. For example, the test results determination zone can include specific binding members such as antibodies, enzymes, enzymatic substrates, coenzymes, enhancers, second enzymes, activators, cofactors, inhibitors, scavengers, metal ions, and the like. One or more of the reagents provided at the test results determination zone can be bound to the test strip material. Test strips including such reagents are known in the art and can be adapted to the test device 500 of the present invention.

In a preferred aspect of the present invention, the one or more analyte detection zones of the test results determination zone include one or more immobilized (covalently or noncovalently immobilized) specific binding members that bind with one or more analytes of interest, such as one or more drugs, hormones, antibodies, metabolites, or infectious agents, when the analytes are also bound by specific binding members bound to a label as are provided in the reagent zone. Thus, in embodiments where the reagent zone contains one or more specific binding members for the analyte, the specific binding members of the reagent zone and analyte detection zone should bind with different epitopes on the analyte being tested for. For example, when a labeled specific binding member in the reagent zone binds with the beta-chain of hCG, when the immobilized specific binding member in the analyte detection zone should bind with another area of hCG, such as the alpha-chain of hCG. Thus, when hCG is present in the sample, the hCG will bind the labeled anti-beta hCG which carried along to the test result determination zone at the analyte detection zone which binds with the immbolized anti-alpha hCG to provide a visual readout at that locus.

The analyte detection zone can include substrates which change in an optical property (such as color, chemiluminescence or fluorescence) when an analyte is present. Such substrates are known in the art, such as, but not limited to, 1,2-phenylenediamine, 5-aminosalicylic acid, 3,3',5,5'-tetramethylbenzidine, or tolidine for peroxidase; 5-bromo-4-chloror-3-indolyl phosphate/nitroblue tetrazolium for alkaline phosphatase and 5-bromo-4-chloro-3-indolyl-beta-D-galactopyranoside, o-nitrophenyl-beta-D-galactopyranoside, napthol-AS-BI-beta-D-galactopyranoside, and 4-methyl-umbelliferyl-beta-D-galactopyranoside for beta galactosidase.

In embodiments where an analyte is detected by a signal producing system, one or more components of the signal producing system, such as enzymes, substrates, and/or indicators, can be provided in the analyte detection zone. Alternatively, the components of the signal producing system can be provided elsewhere in the test strip and can migrate to the analyte detection zone.

Optionally, the test results determination zone can include a control zone. The control zone can be upstream from, downstream from, or integral with the analyte detection zone of the test result determination zone. In the latter case, when analyte and control give a positive reaction, the control zone and analyte detection zone can form an indicia, such as a "+" sign for a positive reaction and a "−" sign for a negative reaction based on the particular format of the assay.

The control zone provides a result that indicates that the test on the test strip has performed correctly. In one preferred aspect of the present invention, the reagent zone includes a specific binding member that binds with a known analyte different from the analyte being tested for. For example, a rabbit-IgG may be provided in the reagent zone. The control zone can include immobilized (covalently or non-covalently) anti-rabbit-IgG antibody. In operation, when the labeled rabbit-IgG in the reagent zone is carried to the test result determination zone and the control zone therein, the labeled rabbit-IgG will bind with the immobilized an anti-rabbit-IgG and form a detectable signal.

The control zone can include substrates which change in an optical property (such as color, chemiluminescence or fluorescence) when a control substance is present.

In one aspect of the present invention, a test strip can include an adulteration control zone that is capable of detecting an adulteration analyte or an adulteration indicator. Such an adulteration control zone can be in addition to or in place of a control zone or a test results determination zone as described herein. In one aspect of the present invention, the test strip can include an adulteration control zone and a control zone and can optionally detect another analyte such as a drug. In the case where a test strip includes an adulteration control zone and a control zone, but does not detect another analyte, the test strip can be used as a separate control strip, which can be provided in a separate channel of a the test platform of the present invention.

The adulteration control zone can detect an analyte using any appropriate method, such as specific binding methods or using chemical detection methods. These types of detection methods are known in the art and are described herein. For example, specific binding methods such as antibody detection methods are described herein. Also, methods to detect an analyte using signal detection methods using chemical or enzymatic methods are also described herein.

Adulteration control zones preferably detect the presence or amount of an analyte that reflects sample adulteration, such as adulteration by dilution, such as substitution or addition of materials from another species, subject or non-human source to a sample or by the addition of an altering agent. Depending on the monitoring of sample acquisition, sample chain of custody and sample preparation, the need for adulteration controls can be different. For example, blood, serum or plasma samples tend to be more difficult for a subject from which such a sample is taken from to adulterate because such samples tend to be drawn by a phlebotomist or other health-care professional and the chain of custody for such samples tend to be relatively rigorous. On the other hand, samples of urine or other bodily fluids tend to be less stringently controlled, but that need not be the case. The choice of adulteration controls can be chosen based on the particular circumstances for sample collection and chain of title as appropriate.

An appropriate adulteration control for different sample types, such as serum, blood, saliva or urine, can be chosen by the skilled artisan. For example, preferred analytes for blood or blood derived sample dilution include but are not limited to hematocrit, protein concentration, hemoglobin (particularly for red blood cell lysis) and analytes for urine or urine derived sample dilution include but are not limited to creatine. Preferred analytes for blood or blood derived sample species include but are not limited to cell-surface antigens or immunoglobulins of any class or subclass, such as IgG, IgM, IgA, IgE or IgD and and analytes for urine or urine derived sample species include but are not limited to cell-surface antigens or immunoglobulins of any class or subclass, such as IgG, IgM, IgA, IgE or IgD and analytes for urine or urine derived sample subject include but are not limited to hormones such as testosterone, estrogen or cell surface antigens. Preferred analytes for adulterants for blood or blood derived samples include but are not limited to pH, hemoglobin and nitrites. Preferred analytes for adulterants include, but are not limited to pH and the adulterants or their derivatives, such as break down products, or derivatives in the sample based on the action of the adulterant, such as the presence or absence of analytes normally present in the sample in the absence of an adulterant or break down products or altered analytes based on the action of an adulterant. Preferred adulterants include, but are not limited to hypochlorite (bleach), chlorine, gluteraldehyde, soap, detergent, Drano (TM), Visine (TM), Golden Seal Tea (TM), citrus products such as juice such as lemon or lime juice, nitrate, Urine Luck (TM) and pyridinium chlorochromate.

Adulteration control zones can be made using methods known in the art and described herein, such as for making a test results determination zone to detect an analyte. The adulteration control zone can be thought of as a test results determination zone for an adulteration analyte and thus the reagent zone can include appropriate reagents for performing an assay for an adulteration analyte. For example, a test strip can include detectably labeled rabbit anti-human IgG and the adulteration control zone can include immobilized goat anti-human IgG antibodies. Thus, in operation of the test strip, the sample adulteration control zone having the detectable label bound thereto would indicate that the sample contains human IgG and thus is presumptively of human origin. If, for example, a supposedly human sample or specimen was used as a sample in such a test strip, the lack of a detectable label in the sample adulteration control zone would indicate that the sample or specimen was not of human origin and thus would not be a valid test. In those circumstances, the test results would indicate that the sample was adulterated, such as providing a sample or specimen from another species or by altering the sample or specimen such that human IgG was degraded or otherwise not present. Adulteration tests can be quantitative or semi-quantitative such that dilution of a sample of human origin would result in a readout having less detectable label than a standard range for undiluted samples. Adulteration tests can be used to detect one or more adulterants in one or more test strips. For example, a single adulteration test strip can detect one or more adulterants.

In one preferred aspect of the present invention, the test strip can include a results determination zone that includes a control zone and a analyte detection zone, and a sample adulteration control zone. In another aspect of the present invention, a test strip can include a results determination zone that optionally includes a control zone, and optionally an adulteration control zone. A second test strip can include an adulteration control zone and optionally a control zone. Preferably, this second test strip includes both an adulteration control zone and a control zone, but that need not be the case. In the instance where one or more first test strips can be used to detect an analyte other than an adulteration analyte and one or more second test strips can be used to detect an adulteration analyte, the test strips can be provided in a single test platform of the present invention, such as a multi-channel test platform.

Orientation of Zones

The various zones of a test strip, including a sample application zone, one or more reagent zones, and one or more test result determination zones, including one or more analyte detection zones and optionally including one or more control zones and one or more adulteration zones, can be on a single strip of material, such as filter paper or nitrocellulose, or can be provided on separate pieces of material. The different zones can be made of the same or different material or a combination of materials, but preferably are selected from bibulous materials, such as filter paper, fiberglass mesh and nitrocellulose. The sample application zone preferably includes glass fibers, polyester or filter paper, the one or more reagent zones preferably include glass fibers, polyester or filter paper and the test results determination zone, including one or more analyte detection zones and optionally including one or more control zones, preferably include nitrocellulose.

Optionally, a fluid absorbing zone is included. The fluid absorbing zone preferably includes absorbant paper and is used to absorb fluid in a sample to drive fluid from the sample application zone through the reagent zone and the detection zone.

Preferably, the zones are arranged as follows: sample application zone, one or more reagent zones, one or more test results determination zones, one or more control zones, one or more adulteration zones, and fluid absorbing zone. If the test results determination zone includes a control zone, preferably it follows the analyte detection zone of the test result determination zone. All of these zones, or combinations thereof, can be provided in a single strip of a single material. Alternatively, the zones are made of different materials and are linked together in fluid communication. For example, the different zones can be in direct or indirect fluid communication. In this instance, the different zones can be jointed end-to-end to be in fluid communication, overlapped to be in fluid communication, or be communicated by another member, such an joining material, which is preferably bibulous such as filter paper, fiberglass or nitrocellulose such as disclosed and depicted in U.S. patent application Ser. No. 09/860408. In using a joining material, a joining material may communicate fluid from end-to-end joined zones or materials including such zones, end-to-end joined zones or materials including such zones that are not in fluid communication, or join zones or materials that include such zones that are overlapped (such as but not limited to from top to bottom) but not in fluid communication.

When and if a test strip includes an adulteration control zone, the adulteration control zone can be placed before or after the results determination zone. When a control zone is present in the results determination zone on such a test strip, then the adulteration control zone is preferably before the control zone, but that need not be the case. In the aspect of the present invention where a test strip is a control test strip for the determination of an adulteration analyte and/or a control, then the adulteration control zone can be placed before or after the control zone, but is preferably before the control zone.

II A Method of Detection an Analyte of Interest

The present invention also includes a method of detecting an analyte of interest in a specimen that includes providing a specimen collection device of the present invention; providing a specimen into the chamber 100; actuating the valve 200 to transfer at least a portion of the specimen from the chamber 100 to the reservoir 300; and contacting the transferred portion of the specimen within the reservoir 300 with a test device 500.

EXAMPLES

Example 1

Manufacture and Construction of the Preferred Device

The chamber 100, valve 200, top part of the reservoir 304, top portion of the base unit 306 may be molded and formed as a single unit from a polypropylene composition. The valve handle 212 with its guiding pin 222 and detachable head 224, the valve plunger 214, the bottom portion of the base unit 306 and the lid 400 may be molded and formed separately from a similar polypropylene composition. The O-rings 220 which are seated around the circumference of the body of the valve plunger 213 are molded and formed of silicone.

The top and bottom portions of the base unit 306 may then be sealed using thermoplastic glue or resin; the valve plunger 214 inserted into the valve body 206 so that the acquisition means is in fluid communication with the first valve orifice. Then the valve handle 212 is slideably inserted into the valve body but only so far as not to slideably engage the valve plunger 214. The lid 400 may then be rotatably mated with the chamber opening 102 and a self adhesive plastic seal arrayed over the opening 314 to protect against contamination and tampering with the reservoir.

Example 2

Use of the Preferred Device for Testing One or More Drug Analytes

The following describes the preferred method of utilizing the integrated sample collection and handling device of the present invention for the detection of drugs of abuse. Preferably a biological specimen such as a urine specimen can be provided directly from a test subject into the chamber 100 through the chamber upper opening 102. Alternatively, the biological specimen can be provided indirectly from a test subject into said chamber 100 such as through the use of a syringe used to withdraw a blood sample from a test subject which sample can then be deposited into the chamber. After deposit of the biological sample into the chamber 100, said chamber upper opening 102 can be rotatably mated and closed by the use of a threaded lid 400 with an O-ring 600 arrayed in a sealably between the upper opening 102 and the threaded lid 400. The threaded lid 400 irreversibly and unidirectionally engages with the sloped projections 112 present on the outer upper surface of the chamber 100 to create a tamper resistant seal. The chamber 100 may additionally be sealed with a tamper evident seal by disposing a plastic heat shrink band around the sealed lid 400 and the upper exposed portion of the chamber 100 and subsequently gently heating the band with a gently heating device such as a hair dryer which shrinks the band.

After the step of providing the specimen into said chamber 100 a temperature sensing device on the chamber side wall 104 can be examined by the testing personnel to verify that the urine specimen is approximately between 95 and 99 degrees Fahrenheit which would indicate that the urine specimen has not been adulterated or tampered with.

FIG. 2(A) shows the valve handle 212 with its guiding pin 222 and detachable head 224 arrayed in the valve piston 204 in the initial shipping position. When arrayed in this initial shipping position the valve handle knob 232 touches the end of cylindrical valve body 206 and the knob location indicator 234 is in the upper most position. In this initial shipping position it can be seen that the valve handle 212 is arrayed in an upright fashion inside of the vertical key slot 226 of the valve piston 204. While the urine specimen is deposited into the chamber and the temperature of the urine specimen is examined, a portion of the urine specimen enters into the valve 200 through the chamber orifice 108 and the first valve orifice 208 and finally collects in the acquisition means 216 of the valve piston 204. The preferred portion of said urine specimen which enters into the valve piston 204 can be at least about one milliliter.

The valve handle 212 with its guiding pin 222 and detachable head 224 is next slideably partially withdrawn from valve piston 204 such that the valve handle 212 clears the vertical key slot 226 of the valve piston 204. As FIG. 2(B) also shows, the valve handle detachable head 224 is too wide to pass through the piston central orifice 230 and so provides a tactile clue by way of a slight resistance which indicates that the valve handle 212 has indeed been withdrawn far enough to clear the vertical key slot 226 of the valve piston 204.

As shown in FIG. 2(C) the valve handle 212 is next rotated in a clockwise fashion one-quarter of the way to a horizontal position so that the valve handle 212 is engaged with the horizontal key slots 228 of the valve piston 204.

Said valve piston 204 may next be actuated by providing a slideable force to the valve handle 212 such that the valve handle 212 engages and slides the valve plunger 214. This force to the valve handle knob 232 should be sufficient to cause the attached valve handle 212 to engage with the horizontal key slots 228 of the valve piston 204 and to move the valve piston in a slideable fashion. FIG. 2(D) shows the displacement of the valve piston 204 part way across the cylindrical valve body 206. In this position the attached acquisition means 216 is in a position in the valve body 206 where the acquisition means is no longer in fluidic communication with the chamber 100. The acquisition means 216 then delivers and dispenses the measured portion of the urine specimen into the reservoir 300 through the second valve orifice 210 such that said portion of the urine specimen is transferred away from said chamber 100 and delivered into said reservoir 300.

FIG. 2(E) shows the valve handle 212 with its guiding pin 222 and detachable head 224 arrayed in the valve piston 204 in the final dispensing position. This final dispensing position is reached when the valve handle knob 232 again touches the end of cylindrical valve body 206. In this final dispensing position, the valve piston 204 is stopped by the valve end wall 236.

The engaging actuation of said valve piston 204 and thus the valve 200 is unidirectional.

Furthermore, the transfer of said measured portion of the urine specimen into the reservoir 300 is irreversible due to the fact that upon an attempted removal or repositioning of the valve piston 204 the detachable head 224 separates from the valve handle guiding pin 222. The separation takes place at a fragile connection 238 located between the detachable head 224 and the guiding pin 222. Upon such separation the valve handle 212 is no longer in slideable engagement with the valve piston 204. FIG. 2(F) shows the separation of the detachable head 224 from the valve handle guiding pin 222. As is evident from the FIG. 2 series of cross sections, at all times of the operation of the specimen collection container the chamber 100 and the reservoir 300 are not in direct fluid communication.

Once the measured portion of the urine sample is delivered to the reservoir 300, the measured portion of the urine sample flows down the sloping channel 310 into the narrow channel 312 of the reservoir 300 where the measured portion of the urine sample resides to be tested with a test device 500 or element such as a test strip. One such test device is an immunoassay test device which identifies the presence of drugs of abuse such as cannabinoids, cocaine, methamphetamine, opiates and phencyclidine. Such an immunoassay test device normally comprises one or more lateral flow test strips for each analyte of interest along with an adulterant determination device. Next a self adhesive plastic seal which has been previously arrayed over the opening 314 to protect against contamination and tampering with the reservoir and the measured portion of the urine sample may be removed and the test device 500 inserted into the opening 314. The testing personnel may then examine the testing device to determine the results of the test conducted on the measured portion of the urine sample and to determine whether possible adulteration of the specimen has taken place.

The test device may then be removed from the reservoir opening 314 and the chamber 100 containing said specimen sealed by sealing the reservoir opening 314 with a cover 700. Thereafter, the sealed chamber 100 can be transported to a laboratory facility for confirmation of test results provided by said test device 500 through at least one additional test.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed:

1. A specimen collection device, comprising:
   (a) a chamber for collecting a specimen;
   (b) a reservoir for receiving an aliquot of specimen from the chamber and for receiving a test device;
   (c) a valve functionally interposed between the chamber and the reservoir and having a compartment for holding an aliquot of specimen and transporting the aliquot from the chamber to the reservoir, the valve having first, second and third positions,
   wherein
   when the valve is in the first position, the valve compartment is in fluid communication with the chamber and is not in fluid communication with the reservoir;
   when the valve is in the second position, the valve compartment is not in fluid communication with the chamber nor the reservoir;
   when the valve is in the third position, the valve compartment is in fluid communication with the reservoir and is not in fluid communication with the chamber; and
   the valve being inoperable after a first actuation.

2. The specimen collection device of claim 1, wherein the device comprises a lid for sealing the chamber.

3. The specimen collection device of claim 2, wherein the lid is a tamper resistant lid or tamper evident lid.

4. The specimen collection device of claim 2, wherein the lid comprises at least one O-ring.

5. The specimen collection device of claim 2, wherein when the chamber is sealed with the lid, the lid does not leak specimen between the chamber and the exterior at an internal pressure of up to 100 pounds per square inch.

6. The specimen collection device of claim 1, wherein the reservoir firmly engages the test device.

7. The specimen collection device of claim 1, wherein the valve is a piston valve.

8. The specimen collection device of claim 1, wherein said valve has at least one valve O-ring.

9. The specimen collection device of claim 1, wherein said valve has two or more O-rings.

10. The specimen collection device of claim 1, wherein the valve does not leak specimen between the chamber and the reservoir at an extcmal pressure of up to 100 pounds per square inch.

11. The specimen collection device of claim 1, wherein the valve includes a handle for actuating the valve, wherein the handle functionally disengages from the valve after the valve is actuated and wherein the valve cannot be actuated with the handle disengaged therefrom.

12. The specimen collection device of claim 1, further comprising at least one test device present in the reservoir.

13. The specimen collection device of claim 12, wherein the test device comprises at least one test strip.

14. The specimen collection device of claim 13, wherein the test strip comprises reagents for performing at least one specific binding reaction.

15. The specimen collection device of claim 13, wherein the test strip comprises reagents for an immunoassay.

16. The specimen collection device of claim 13, wherein the test strip comprises reagents for an enzymatic reaction.

17. The specimen collection device of claim 13, wherein the test strip comprises reagents for a chemical reaction.

18. The specimen collection device of claim 1, wherein the reservoir comprises a port for receiving the test device.

19. The specimen collection device of claim 1, wherein the test device comprises an adulteration determination device.

20. The specimen collection device of claim 1, wherein the specimen is a liquid specimen.

21. The specimen collection device of claim 1, wherein the specimen is a biological specimen.

22. A method of detecting an analyte of interest in a specimen, comprising:
   a) collecting a specimen in a test device comprising;
      i) a chamber for collecting and holding the specimen;
      ii) a reservoir for receiving an aliquot of specimen and having a test device; and
      iii) a valve functionally interposed between the chamber and the reservoir and having a compartment for holding the aliquot, and having a first position wherein the compartment is in fluid communication with the chamber, and a second position wherein the compartment is separated from fluid communication with both the chamber and the reservoir, wherein the valve is inoperable after a first actuation;
   b) causing an aliquot of specimen to enter the compartment of the valve;
   c) actuating the valve;
   d) causing the aliquot of specimen to flow out of the compartment and into the reservoir to contact the test device; and
   e) detecting the analyte of interest.

23. The method of claim 22 wherein actuation of the valve comprises causing the valve to move from the first to the second position, and then to a third position where the compartment is in liquid communication with the reservoir and is not in liquid communication with the chamber.

24. The specimen collection device of claim 22 wherein the test device comprises a test strip having reagents for detecting the presence of at least one analyte of interest.

25. The method of claim 22 wherein the test device comprises a test strip comprising reagents for conducting an immunoassay.

26. The method of claim 25 wherein after the specimen aliquot contacts the reagents for conducting an immunoassay, visible indicators become present on the test strip indicating the presence or absence of the analyte of interest.

27. The method of claim 22 wherein the specimen is a biological specimen.

28. The method of claim 22 wherein the analyte of interest is selected from the group consisting of: a drug of abuse, a hormone, a protein, a nucleic acid molecule, an etiological agent and a specific binding member.

* * * * *